(12) United States Patent
Oettgen et al.

(10) Patent No.: US 6,960,444 B2
(45) Date of Patent: Nov. 1, 2005

(54) TRANSCRIPTIONAL MEDIATORS OF BLOOD VESSEL DEVELOPMENT AND ENDOTHELIAL DIFFERENTIATION

(75) Inventors: Peter Oettgen, Brookline, MA (US); Towia Libermann, Newton, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 10/446,468

(22) Filed: May 28, 2003

(65) Prior Publication Data

US 2004/0091468 A1 May 13, 2004

Related U.S. Application Data

(63) Continuation-in-part of application No. PCT/US01/44586, filed on Nov. 28, 2001.
(60) Provisional application No. 60/253,566, filed on Nov. 28, 2000.

(51) Int. Cl.[7] .......................... G01N 33/53; C07K 14/00
(52) U.S. Cl. .......................... 435/7.1; 530/350; 530/399
(58) Field of Search ........................... 435/7.1; 530/350, 530/399

(56) References Cited

U.S. PATENT DOCUMENTS 5,721,113 A * 2/1998 Libermann et al. ........ 435/69.1

OTHER PUBLICATIONS

Leiden et al. 1992, J. Virol. 66 (10): 5890–5897.*

Nishiyama et al. 2000, BioSci. Biotechnol. Biochem. 64 (12): 2601–2607.*

Thompson et al. 1992; Mol. Cell. Biol. 12 (3): 1043–1053.*

* cited by examiner

*Primary Examiner*—Karen Cochrane Carlson
(74) *Attorney, Agent, or Firm*—Edwards & Angell, LLP; David G. Conlin; Gregory B. Butler

(57) ABSTRACT

This invention relates to methods of modulating the development of blood vessels and/or endothelial cell differentiation in a mammal comprising altering the activity of an Ets transcription factor, which activates vascular specific genes. More particularly, the transcription factor comprises ELF-1, and transcription factors that are homologous to ELF-1. The invention further relates to methods of screening for compounds that affect the activity of these transcription factors, and therefore, affect the development of blood vessels and/or endothelial cell differentiation. The invention also relates to methods of using these compounds to treat diseases, or symptoms of diseases, by either increasing or decreasing blood vessel development and/or endothelial cell differentiation.

27 Claims, 14 Drawing Sheets

```
cELF-1- MAAVVQQNELVFEFASNVMEDEQQLGDPSIF              DOMAIN A
                                    PAVLVEVVKSGDLLNNY
hELF-1- --------D-------------R-----A--            -I---S-
mELF-1- --------D--------G----------A--            -I---S-

DOMAIN B
SGLTCVDEPSDMITENSL DVAFLSFQHPDDDIPLTVELSG NGDETME
A--A--E--N-----S-- ---------------------- D----I-
A--A--E--N-----S-- ----------------A----- -----I-

DOMAIN C
FLDAVAEGLHMDSR GP MLDEKRITAM-FGSTEDEDIVAPITHVSVTL
-------NS----       --------NNNI-S-P--DMV---V-------
------MLC----S-PV----Q-NNNI-S-S--D_-----------

DOMAIN D
DGIPEVVEVHQAPDPYSETPETPEFEQP KKKNGKKPKP SRPESPTTTP
------M-TQ-VQEK-ADS-GASSP---  RKERNTS  -P--D--A---
------M-TQ-VQETNADS-GASSP--R  RPENTN   -P--D------

NISVKK QNKDKQGNPEDWDRLLALSQDKATQPKYTQKWTQREKGTPKLVDSKAV
------
------

SPLWGKHKNQPDMNYETMGRALRYYYDRGTIAKVEGQRLVYQFKEMPKDLVYID
                                                  --I-N
                                                  --I---

DEDASPSTESSDSSLLSTPVASRNQSSRSRASANTGTKGGSTTVLKTGNSK
---P-S-I----P--S-S_ASN---T----V-SSP-V---A-----P----
---P-S-I----Q--S--TAS----AN---V-SSP-I---AA-I--P----

PAKLKEHVEVVQQQTPGLTSEVLRTMQSTQ        PVHPTQLFRTVH
A--P-DP---A-P_         ------V-P--SPYPTQLFRT--VV-------
A-NP-DP---G-P_         ------V-PS-APYPTQLFRT--VV-------

VMQPLHTLTEGHAAVTSNVPDETLNPSVQNIRTLQTPTQVPVVVSPGNQQL
----VQAVP--E--R--TMQ-----S---S---I-A--------------
----VQAVP-_E-TIA-TMQE-AA-S--PS---I-AS-------------

HTVTLQTVPLTTVIASTDPASAATPQKFILQAIPTSPPMTVLKENVMLQSQ
-------------------SAGTGS---------S---------------
----_---------I--S-G-GS------T--S-----------------

KPVSPPSSIVLSPAQVQQVLTSSVQTICNGTANVASSPSFAATTPVVTFSP
-AG----_---G----------N--------VS-------S--A-G-----
--G-_--_-----T--------N--S----AGS---A---S--A------_

SSSQVVAHPSGTVITSVIKATEAKQIGVQGVLKEDDGDKLDDPEQSEQRFQ
R---L----P---------TQ-T-TLT_-E-E-KESE-H-KENTEK_TEQ-
R---L----P---------KQ-T-TLT_-E-E-K_AE-D-NEDAEK_SAQ-

QQPFVMVVSSSNSFPSNIQAKQENEPLEPNSY
P--Y--------G-T-QVAM--_--L-----F
P--Y---L----G-S-QVAV--_--L-----F
```

Fig. 1

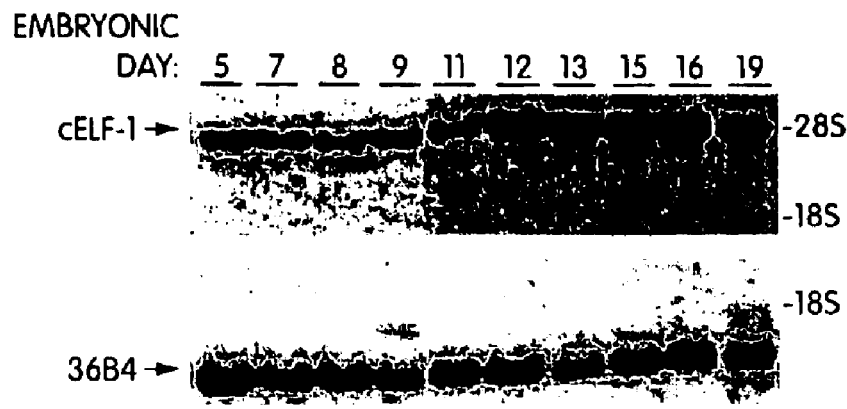
Fig. 3A
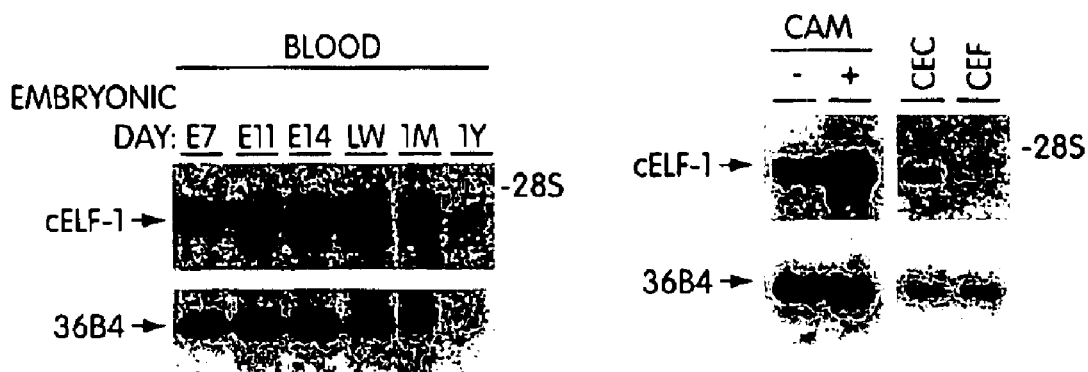
Fig. 3B
Fig. 3C
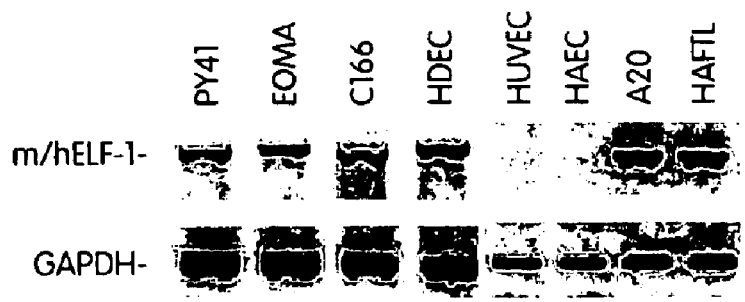
Fig. 3D

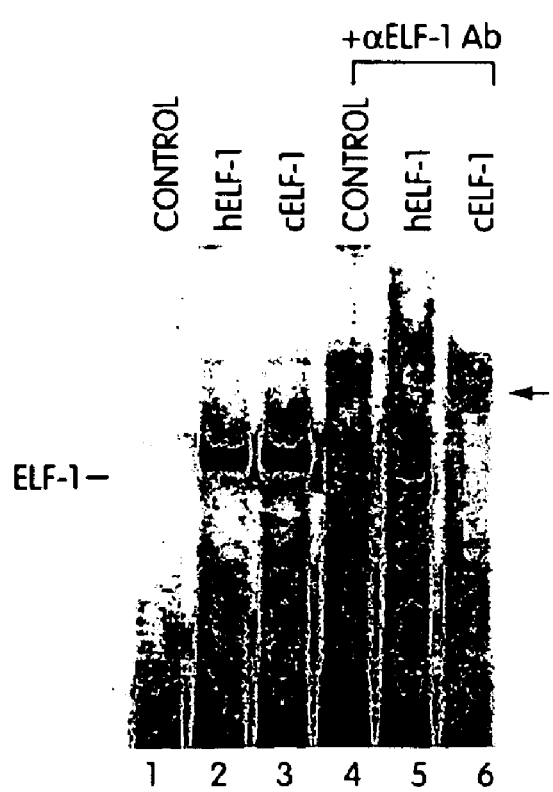
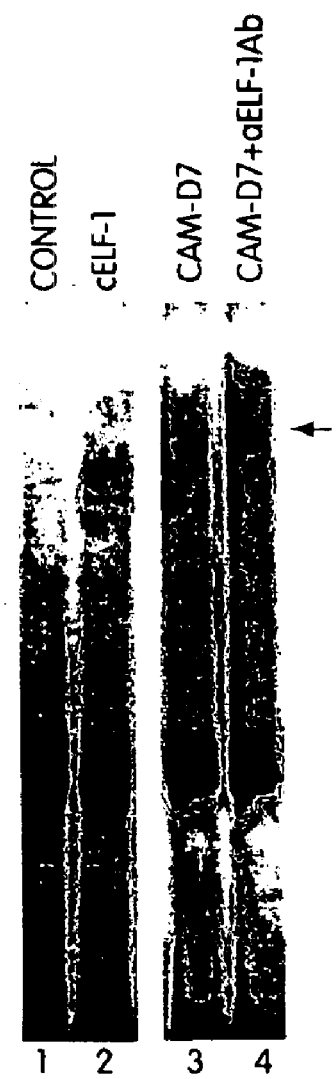
Fig. 8A
Fig. 8B

TRANSCRIPTIONAL MEDIATORS OF BLOOD VESSEL DEVELOPMENT AND ENDOTHELIAL DIFFERENTIATION

RELATED APPLICATION

This application is a continuation-in-part of International Application Ser. No. PCT/US01/44586, filed Nov. 28, 2001, which claims the benefit of U.S. Provisional Application Ser. No. 60/253,566, filed Nov. 28, 2000. The entire contents of each of these application is incorporated herein by this reference.

GOVERNMENT SUPPORT

This work describes herein was supported by a grant from the National Institutes of Health (Grant No. RO1-HL63008). Therefore, the U.S. Government may have certain rights in the invention.

FIELD OF THE INVENTION

This invention relates to methods of modulating the development of the blood vessels and/or endothelial differentiation in a mammal comprising altering the activity of an Ets transcription factor which activates vascular specific genes. More particularly, the transcription factor comprises ELF-1, and transcription factors that are homologous to ELF-1. The invention further relates to methods of screening for compounds that affect the activity of these transcription factors, and therefore, affect the development of blood vessels. The invention also relates to methods of using these compounds to treat diseases, or symptoms of diseases, by either increasing or decreasing blood vessel development and/or endothelial differentiation.

BACKGROUND OF THE INVENTION

Vasculogenesis, the development of new blood vessels, begins during the second week of normal human embryogenesis. Vascular development requires the tightly coordinated expression of several growth factors and their receptors. Among these are the Tie1 and Tie2 receptors which are almost exclusively endothelial cell specific. The critical transcriptional regulators of vascular-specific gene expression remain largely unknown.

Vascular development involves a complicated series of events including stem cell differentiation in developing embryos, endothelial cell interactions, and endothelial cell proliferation in developing tissue and in pre-existing endothelial cells, e.g., in angiogenesis. In an example of endothelial cell interaction, blood vessel development requires endothelial cells interact with surrounding mesenchymal cells for proper vessel development.

Angiogenesis may have beneficial or deleterious effect, depending on the circumstances in which is arises. For example, angiogenesis is a critical component of a number of diseases, in which it can have either beneficial or deleterious effects. The generation of new capillaries is necessary for normal healing in wound repair. In acute and chronic coronary ischemia the development of collateral blood vessels is a beneficial effect of angiogenesis. Examples of harmful effects of angiogenesis include neovascularization which results in diabetic retinopathy, and angiogenesis-dependent growth of many tumors.

Angiogenesis begins when clusters of endothelial cells fuse into cellular chords and eventually tubes, thus creating the new blood vessel. This process recapitulates the events that occur during embryonic blood vessel development.

There has been considerable interest in identifying factors that regulate blood vessel development. Several growth factors have received a great deal of attention as regulators of endothelial cell differentiation and angiogenesis. An angiogenic growth factor that is highly expressed during embryogenesis, and appears to have unique target cell specificity for vascular endothelium is vascular endothelial growth factor (VEGF). Furthermore, its receptors Flk-1 and Flt-1 are expressed on the surface of developing and mature mouse blood vessels.

Tie1 and Tie2 are another family of endothelial-specific receptor tyrosine kinases which have been determined to be critical for vascular development. (Sato, T. N., et al., 1993. Proc Natl Acad Sci USA 90:9355–8). They are expressed predominantly on endothelial cells of the developing vasculature. Targeted disruption of Tie1 leads to the development of leaky blood vessels resulting in edema and hemorrhage, while disruption of Tie2 leads to dilated blood vessels and abnormal capillary networks, and early embryonic death (Sato, T. N., et al., 1995. Nature 376:70–4). The growth factor ligand for the Tie2 receptor, angiopoietin-1, has been recently identified (Davis, S., et al., 1996. Cell 87:1161–9). Mutations in the Tie2 gene have been identified in humans, resulting in venous malformations (Vikkula, M., et al., 1996. Cell 87:1181–90). Tie1 and Tie2 gene expression has been shown to be upregulated during tumor angiogenesis (Hatva, E., et al., 1995. Am J Pathol 146:368–78; Kaipainen, A., et al., 1994. Cancer Res 54:6571–7). Although these receptors were described as being completely endothelial cell specific it has recently been shown that both receptors are expressed in up to 30 percent of undifferentiated hematopoietic stem cells and 10 percent of B cells, suggesting a possible role in hematopoiesis in addition to vasculogenesis (Hashiyama M, et al. Blood. 1996;87:93–101; Yano M, et al. Blood. 1997;89:4317–4326).

Although much information has emerged concerning the possible role of growth factors and their receptors during vascular development, little is known about the nuclear events that orchestrate this process at the transcriptional level.

The Ets genes are a family of at least thirty members that function as transcription factors and play a central role in regulating genes involved in development, cellular differentiation and proliferation. Interestingly, the main regulatory elements of the Flt-1, Tie1, and Tie2 genes have several conserved putative Ets binding sites, which are critical for the transcriptional activity of the promoters and enhancers of these genes. For example, a mutation of one Ets binding site in the promoter of the Flt-1 gene leads to a ninety-percent reduction in the basal activity of the promoter. Likewise, in transgenic animals in which LacZ expression is directed throughout the vasculature by the Tie2 promoter and enhancer, a mutation in an Ets binding site in the core enhancer leads to a marked reduction in vascular directed LacZ gene expression. It is currently unknown, which of the Ets factors are critical for the transcriptional activity of these genes.

Thus, it would be useful to be able to regulate blood vessel development and/or endothelial cell differentiation in order to treat certain types of diseases that involve vascular development. For example, it would be useful to block blood vessel development, i.e., angiogenesis, in diseases such as certain cancers, diabetic retinopathy and inflammation, e.g., rheumatoid arthritis. Currently, however, the ability to block angiogenesis in a variety of diseases remains incomplete. The major shortcomings of the currently available antiangiogenesis drugs are that they may not completely block angiogenesis. The identification of novel angiogenesis inhibitors, especially those that offer a more complete means of blocking angiogenesis, is highly desirable.

Furthermore the ability to increase blood vessel development to treat certain diseases, or symptoms of certain diseases, is highly desirable. For example, known compounds that induce blood vessel development for treating certain diseases, e.g., in coronary heart disease and after myocardial infarction, are limited, and the discovery of small molecules or novel proteins that could enhance the ability to enhance angiogenesis in these disease states is also highly desirable.

SUMMARY OF THE INVENTION

The development of new blood vessels occurs during normal development. It is also a critical component of several diseases where it can have beneficial or deleterious effects. The process of blood vessel development involves the tightly regulated expression of several growth factors and their receptors. We have identified transcription factors that are critical regulators of these genes and may serve as "master switches" of this process. The present invention relates to the use of these factors in regulating blood vessel development, endothelial cell differentiation, angiogenesis and endothelial function. Thus, the methods of the present invention provide a much more powerful therapeutic approach for regulating blood vessel development in a positive or negative way than expressing or delivering an individual gene or protein.

The present invention relates to a method of controlling blood vessel development in a mammal comprising altering the activity of an Ets transcription factor which activates vascular specific genes, wherein the transcription factor comprises ELF-1, or transcription factors that are homologous thereto, and wherein decreasing the activity of the transcription factor decreases blood vessel development and increasing the activity of the TF increases blood vessel development. In preferred embodiments of the present methods, the transcription factor is selected from the family of Ets transcription factors, particularly a subset which has at least about 30% homology to the amino acid sequence of the ETS domain (i.e., the DNA binding domain) of ELF-1 or NERF. In certain embodiments the transcription factor is selected from a subset which has at least about 30%40% homology to the amino acid sequence of the ETS domain of ELF-1.

Examples of possible Ets transcription factors include ETS-1, ETS-2, ER71, ERG, FLI-1, ETS-3, FEV, ETS-6, ERF, PE-1, GABP-alpha, ER81, ETV1, ERM, PEA3, EIAF, PU.1, Spi-B, TEL, TEL2, PDEF, ESE-1, ESE-2, ESE-3, ERP, SAP-1, and ELK-1, provided they have at least about 30%–40% homology to the amino acid sequence of the ETS domain of ELF-1.

Preferably the transcription factor has an Ets domain that has at least about 70% homology to the amino acid sequence of the Ets domain of ELF-1. Examples of such transcription factor include ELF-1, NERF and MEF, cELF-1, and functional equivalents thereto. In preferred methods of the present invention, the transcription factor comprises ELF-1. The methods and products of the present invention will be described with reference to this subset of Ets transcription factors, and ELF-1 in particular. However, it is to be understood that the invention is not limited thereto. Other transcription factors may also be useful in the present invention. Furthermore, it is to be understood that such reference to the transcription factors, e.g., the ELF-1 polypeptide, refers to naturally occurring and non-naturally occurring peptides and variants thereto. One of ordinary skill in the art can readily determine useful variants of the polypeptides.

The present invention relates to a method of controlling blood vessel development in a mammal comprising altering the activity of an Ets transcription factor which activates vascular specific genes, wherein the transcription factor comprises ELF-1, and transcription factors that are homologous thereto, and wherein decreasing the activity of the transcription factor decreases blood vessel development and increasing the activity of the TF increases blood vessel development. In preferred methods, the transcription factor has at least about 30% homology to the amino acid sequence of the ETS domain of ELF-1. In certain embodiments the transcription factor is selected from a subset which has at least about 30%–40% homology to the amino acid sequence of the ETS domain of ELF-1. Preferably the transcription factor has an Ets domain that has at least about 70% homology to the Ets domain of ELF-1. Examples of such transcription factor include NERF and MEF, and functional equivalents thereto.

The methods of the present invention are useful for controlling all type of blood vessel development, e.g., vasculogenesis, angiogenesis and the differentiation of endothelial cells from pluripotent stem cells.

In certain methods of the present invention decreasing the activity of the transcription factor further comprises either decreasing the function of the transcription factor or blocking the expression of the transcription factor. One of ordinary skill in the art would readily be able to determine methods of blocking the expression of the transcription factor. However, one example of blocking the expression of the transcription factor comprises inhibiting the activation of the promoter for the gene encoding the transcription factor. Similarly, methods of inhibiting activation of the promoter are readily selected. An example of methods of inhibiting activation further comprises providing a substance that blocks the function or expression of the transcription factor.

In other methods of the present invention, altering the activity of the transcription factor comprises increasing the activity of the transcription factor. In certain methods, the step of increasing the activity of a transcription factor comprises either increasing the function of the transcription factor or increasing the expression of the transcription factor. In still further embodiments, the step of increasing activity further comprises providing a substance that increases the function or expression of the transcription factor.

The substance used in the present methods to increase or decrease the activity of the transcription factor can be readily selected by those of ordinary skill in the art. In certain methods of the invention, e.g., the substance used to increase or decrease the activity of the transcription factor is selected from the group consisting of small molecules, peptides, dominant negative mutants, antisense RNAs, or DNA viruses. Certain methods of the present invention further comprise providing the substance systemically to the mammal, or, alternatively, locally to the site of blood vessel development.

The present invention also relates to methods of increasing blood vessel development where the step of increasing the function of the transcription factor comprises providing additional transcription factor to the mammal at the site of desired blood vessel development. Such methods can be used for treating diseases where it is desirable to increase blood vessel development, including, but not limited to, coronary heart disease, ischemia, poor circulation, peripheral vascular disease or cerebral vascular disease.

The present invention also relates to methods of decreasing blood vessel development and/or endothelial differentiation for treatment of diseases in which it is desirable to decrease such development. Examples of such disease include, but are not limited to, cancer, diabetic retinopathy, inflammation in joints of patients with rheumatoid arthritis, localized inflammation, psoriasis, or inflammatory bowel disease.

The present invention also relates to methods of screening compounds that are capable of increasing blood vessel development and/or endothelial differentiation comprising: (a) providing cells that do not normally express a measurable amount of a transcription factor having at least about 30% homology to the amino acid sequence of the ETS domain of ELF-1, (b) transfecting the cells with a vector comprising the transcription factor or functional equivalent thereof; (c) providing to a portion of the cells a compound to be screened; (d) providing a portion of the cells as a control without the compound; (e) measuring the expression of the transcription factor in the cells, and (f) comparing the amount of expression of the transcription factor in the cells containing the compound with the control portion of cells, wherein expression in (c) greater than expression in (d) indicates a compound that increases blood vessel development. In certain embodiments the transcription factors has at least about 70% homology amino acid sequence of the ETS domain of ELF-1. Examples of useful transcription factors comprise ELF-1, NERF or MEF. In preferred screening methods the cells comprise endothelial cells or embryonic stem cells. Examples of useful endothelial cells include, but are not limited to human umbilical endothelial cells (HUVECs), human aortic endothelial cells (HAEC), dermal endothelial cells or coronary endothelial cells. The present methods screen for compound, e.g., small molecules, peptides, dominant negative mutants, antisense RNAs or viral DNAs.

The methods of the present invention are useful for controlling all type of blood vessel development and angiogenesis and the differentiation of stem cells into endothelial cells.

The present invention also relates to methods of screening compounds that are capable of decreasing blood vessel development and/or endothelial differentiation comprising: (a) providing cells which do not normally express a measurable amount of a transcription factor which has at least 30% homology to the ETS domain of ELF-1; (b) transfecting the cells with a vector comprising the transcription factor or functional equivalent thereof; (c) providing to a portion of the cells a compound to be screened; (d) providing a portion of the cells as a control without the compound; (e) providing a proangiogenic compound to the cells in (c) and (d); (f) measuring the expression of the transcription factor in the cells, and (g)comparing the amount of expression of the transcription factor in the cells containing the compound with the control portion of cells, wherein expression in (c) less than expression in (d) indicates a compound that decreases blood vessel development. In certain embodiments the transcription factors has at least about 70% homology to the amino acid sequence of the ETS domain of ELF-1. Examples of useful endothelial cells include, but are not limited to HUVECs, HAEC, HDEC, dermal endothelial cells or coronary endothelial cells. The present methods screen for compound, e.g., small molecules, peptides, dominant negative mutants, antisense RNAs or viral DNAs.

The present method also relates to a method of screening compounds that are capable of decreasing blood vessel development and/or endothelial cell differentiation comprising: (a) providing cells which express a measurable amount of a transcription factor which has at least 30% homology to the ETS domain of ELF-1; (b) providing to a portion of the cells a compound to be screened; (c) providing a portion of the cells as a control without the compound; (d) providing a proangiogenic compound to the cells in (b) and (c); (e) measuring the expression of the transcription factor in the cells; and (f) comparing the amount of expression of the transcription factor in the cells containing the compound with the control portion of cells, wherein expression in (b) less than expression in (c) indicates a compound that decreases blood vessel development. In certain embodiments the transcription factors has at least about 70% homology to the amino acid sequence of the ETS domain of ELF-1. In certain embodiments, the cells comprise cells from blood vessels in CAM, tumor cell models of angiogenesis in nude mice. The present methods screen for compound, e.g., small molecules, peptides, dominant negative mutants, antisense RNAs or viral DNAs.

The present invention also relates to a method of diagnosing the presence of a disease that causes angiogenesis in a mammal comprising: (a) removing a sample from the mammal and (b) measuring the presence of an Ets transcription factor wherein the transcription factor is not present in detectable amounts in the sample in the absence of the disease. In preferred methods, the transcription factor comprises a transcription factor that is homologous to ELF-1. In yet preferred methods, the transcription factor has a greater than about 30% homology to the ETS domain of ELF-1. In certain embodiments, the transcription factor has an Ets domain that has at least about 70% homology to the Ets domain of ELF-1. Examples of preferred transcription factors include NERF, ELF-1 or MEF. Such methods are useful for diagnosing diseases, such as, but not limited to, cancer, inflammation, diabetic retinopathy, inflammation in joints of patients with rheumatoid arthritis, localized inflammation, psoriasis or inflammatory bowel disease. In certain methods, the sample comprises tissue, synovial fluid, urine, CSF or blood.

The present invention also relates to a method of decreasing blood vessel development and/or endothelial differentiation to treat a disease comprising decreasing the expression of a vascular-specific gene by decreasing the activity of a transcription factor that is homologous to ELF-1, wherein the step of decreasing the activity of the transcription factor further comprises either decreasing the function of the transcription factor or blocking the expression of the transcription factor.

The present invention also relates to a method of increasing blood vessel development and/or endothelial differentiation to treat a disease comprising increasing the expression of a vascular-specific gene by increasing the activity of a transcription factor that is homologous to ELF-1, wherein the step of increasing the activity of the transcription factor further comprises either increasing the amount or function of the transcription factor or increasing the expression of the transcription factor.

In preferred embodiments of these methods, the transcription factor has a greater than about 30% homology to ELF-1. In certain embodiments the transcription factors has at least about 30–40% homology amino acid sequence of ELF-1. In other certain methods, the transcription factor has an Ets domain that has a greater than about 70% homology to the Ets domain of ELF-1. Examples of the transcription factor include NERF, ELF-1 or MEF. Examples of vascular specific genes include, but are not limited to, Tie1 gene, Tie2 gene, FLK-1 gene or FLT-1 gene.

The present invention also relates to pharmaceutical compositions for modulating blood vessel development and/or endothelial cell differentiation comprising a compound that alters the expression of an Ets transcription factor that is homologous to ELF-1, and a pharmaceutically acceptable carrier. Examples of transcription factors include ELF-1, NERF or MEF. Preferably the compound is a small molecule, peptide, or antisense RNA. The compound either increases the expression of the transcription factor and therefor increases blood vessel development, or alternatively, decreases the expression of the transcription factor and therefor decreases blood vessel development.

The present invention also relates to a method of increasing blood vessel development and/or endothelial differentiation comprising increasing the activity of a transcription factor, wherein the transcription factor is homologous to ELF-1 and is either not expressed in diseased tissue or expressed in low amounts. The term "low amount" refers to the transcription factor being present in an amount that is not sufficient to obtain the desired result. For example, even if the transcription factor is present it may be desirable to increase the blood vessel development in that area, increase angiogenesis. In such a case, it is desirable to increase the activity, amount and/or function of the transcription factor to increase blood vessel development. Preferably the transcription factor is selected from ELF-1, NERF or MEF. In certain embodiments, the step of increasing the activity of the transcription factor comprises increasing expression, activity or amount of the transcription factor, or a combination of one or more of the three.

The present invention relates to an isolated polynucleotide having the nucleotide sequence set forth in FIG. 1 (cEFL-1, SEQ ID NO. 2). The present invention also relates to an isolated polynucleotide encoding a polypeptide having transcriptional regulatory activity selected from the group consisting of: (a) a polynucleotide encoding cELF-1 having the nucleotide sequence as set forth in FIG. 1 (SEQ ID No. 2); (b) a polynucleotide which hybridizes to the complement of a polynucleotide according to (a) and is about 90% identical; and (c) a degenerate polynucleotide according to (a) or (b). The invention also relates to a polynucleotide which is DNA or is RNA. The invention also relates to a vector comprising the DNA and a recombinant host cell comprising the vector. The invention also relates to a method for preparing essentially pure cELF-1 protein comprising culturing the recombinant host cell as described above under conditions promoting expression of the protein and recovery thereof.

BRIEF DESCRIPTION OF THE FIGURES

FIG. 1 shows the complete protein sequence for cELF-1 (SEQ ID NO. 2) in comparison to the mouse (m) (SEQ ID NO: 3) and human (h) (SEQ ID NO. 1) counterparts. Dash(-) represents identity to amino acid, and underline(_) signifies amino acid not present in this position.

FIG. 3(A) shows Northern blot analysis of cELF-1 expression of in microdissected blood vessels from the chicken CAM at different developmental stages(Day 5 through 19) Control is 36B4, a chicken housekeeping gene. FIG. 3(B) shows Northern blot analysis of chicken fetal blood at different developmental stages. FIG. 3(C) shows expression of cELF-1 in CAM derived blood vessels washed free of blood (−) compared to with blood(+), and cELF-1 expression in chicken yolk sac endothelial cells and embryonic fibroblasts.

FIG. 3(D) shows RT-PCR for expression of murine and human ELF-1 in human and murine endothelial cells. PY41 and EOMA (endothelioma cell lines), C166, a murine endothelial yolk sac endothelial cell line, human dermal microvascular endothelial cells(HDEC), human umbilical endothelial cells (HUVECs), human aortic endothelial cells (HAEC), and two B cell lines; HAFTL and A20.

FIG. 6(A) shows cELF-1 expression is detected in the endothelium of the dorsal aorta (DA) of E4 chickens. FIG. 6(B) shows a higher magnification of A viewed with 40× objective. Arrows point to endothelial lining of dorsal aorta. Arrowhead indicates expression of cELF-1 by blood cells. FIGS. 6(C,D) show negative control staining with similar concentrations of preimmune serum. FIG. 6(E) shows inner endothelium lining of E5.5 chicken blood vessel (arrow). FIG. 6(F) shows arrowheads pointing to the intersomitic vessels of E4 chicken. FIG. 6(G) shows the presence of cELF-1 in E4 heart (H) but not surrounding lung (L). Figure g (H) shows a higher magnification (20×) of chicken embryo heart. Arrow indicates pericardium while arrowhead depict endocardium

FIG. 8(A) shows an electrophoretic mobility shift assay (EMSA) of in vitro translated cELF-1 compared to human ELF-1 with an oligonucleotide probe encoding the Tie2 Ets sites (lanes 1–3). The control is an in vitro translation with the empty expression plasmid. This is followed by addition of an ELF-1 specific antibody(lanes 4–6). Black arrow denotes supershift. FIG. 8(B) shows EMSA using the Tie2 Ets probe and chicken CAM cell extracts at day 10 alone or with the anti-ELF-1 antibody (lanes 3,4) compared to in vitro translated control and cELF-1 (lanes 1 and 2).

DETAILED DESCRIPTION OF THE INVENTION

Figure 2:
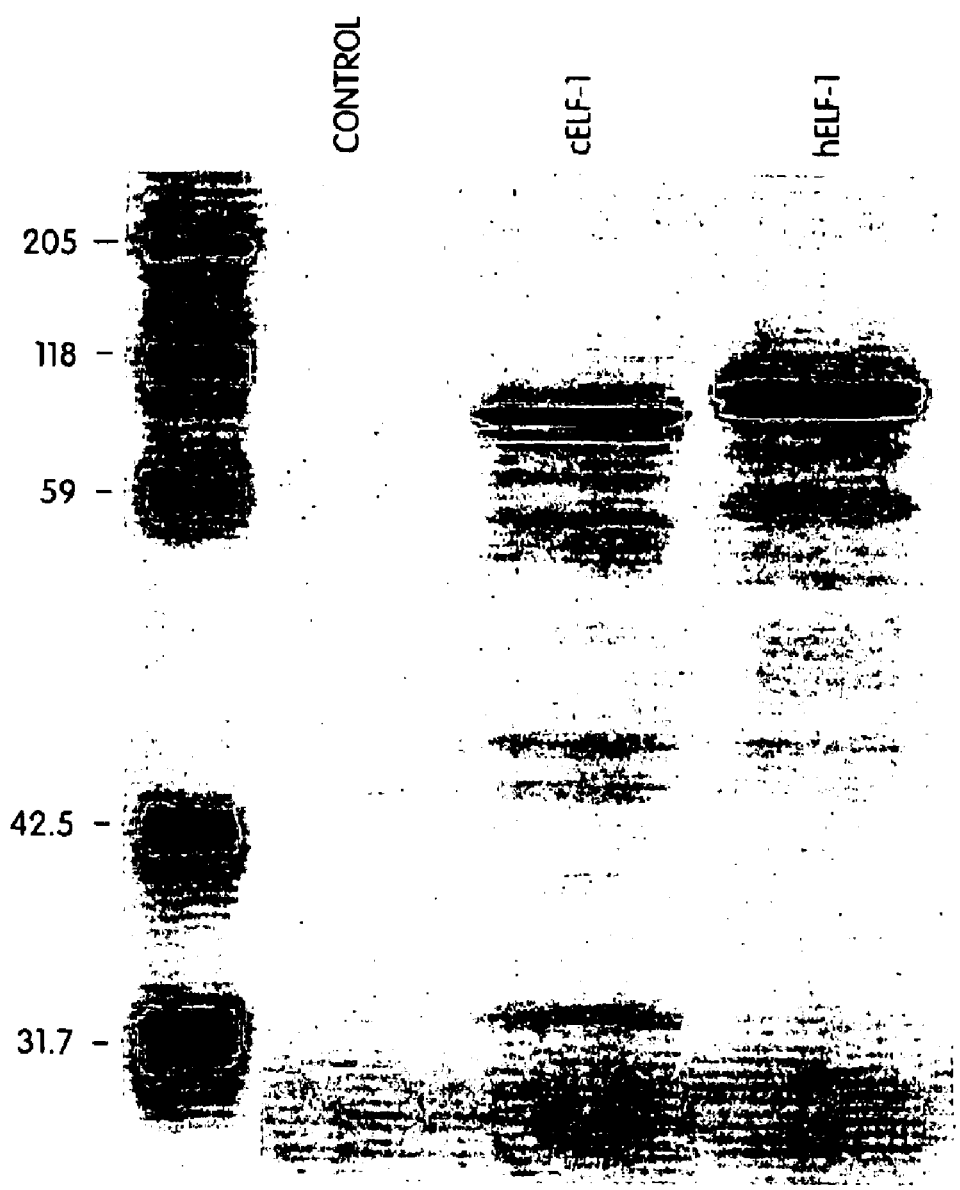
FIG. 2 shows $S^{35}$-methionine in vitro translated cELF-1 protein in comparison to human ELF-1. Molecular weight standard sizes in Kd are shown on the left.

Definitions:

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

Examples of the substantial equivalent amino acid sequence to the amino acid sequence represented by ELF-1 in FIG. 1 (herein after referred to as SEQ ID NO. 1) are an amino acid sequence of not less than about 70% identity to the amino acid sequence represented by SEQ ID NO. 1 and so on. Examples of the protein comprising a substantial equivalent to the amino acid sequence represented by ELF-1 are a protein which comprises a substantial equivalent amino acid sequence to the amino acid sequence represented by SEQ ID NO. 1 and has a substantial equivalent activity to the protein comprising the amino acid sequence represented by SEQ ID NO. 1, and so on. Examples of the substantial equivalent activity include a transcriptional activity of ELF-1 of the present invention, e.g., the ability to transactivate the Tie2 promoter. The term "substantial equivalent" means that the nature of these activities are equivalent. Therefore, it is preferred that the strength of these activities is equivalent (e.g. about 0.1 to about 100 times, preferably about 0.5 to about 10 times, more preferably about 0.5 to about 2 times), and it is allowable that even differences among grades such as the strength of these activities and molecular weight of the protein are present. The activity of the molecules may be measured by per se known methods. For example, they may be measured by the method for screening as mentioned below.

The proteins of the present invention include mutants such as proteins comprising (1) an amino acid sequence wherein 1 or more amino acid residues (for example 1 to 30, preferably 1 to 10, more preferably a few amino acid residues) are deleted from the amino acid sequence represented by SEQ ID NO. 1; (2) an amino acid sequence wherein 1 or more amino acid residues (for example 1 to 30, preferable 1 to 10, more preferable a few amino acid residues) are added to the amino acid sequence represented by SEQ ID NO. 1, (3) an amino acid sequence wherein 1 or more amino acid residues (for example 1 to 30, preferably 1 to 10, more preferably a few amino acid residues) in the amino acid sequence represented by SEQ ID NO. 1 are substituted with one or more other amino acid residues, or (4) combinations thereof.

The term "homology" as used herein refers to the degree of similarity between ELF-1 and other useful transcription factors. One of ordinary skill in the art can readily determine the degree of homology of a transcription factor to ELF-1 by methods known in the art. See e.g., Oettgen et al., Mol. Cell. Biol. Vol 16., No. 9, September 1996, p. 5091–5106. See also the description of "substantial similarity" in U.S. Pat. No. 5,721,113.

The methods of the present invention modulate the activity of certain transcription factors that are involved in blood vessel development or endothelial differentiation. Preferred transcription factors include a subset of Ets transcription factors that are homologous to ELF-1 and include NERF (and NERF isoforms, e.g., NERF1A and 1B and, in particular, NERF 2A and 2B)) and MEF, and their substantial equivalents. The sequence of ELF-1 is described elsewhere (see Leiden, J. M., et al, *J. Virol.* 66:5890–5897; Oettgen, P., et al., *Mol. Cell. Biol., September* 1996, Vol. 16, No. 9, p. 5091–5106.) One of ordinary skill in the art can readily select appropriate transcription factors for use in the methods, based upon the knowledge available in the art and the teachings described herein.

The term "blood vessel development" includes all types of blood vessel development including vasculogenesis and angiogenesis, differentiation of embryonic stem cells into endothelial cells, endothelial cell interactions (e.g., with surrounding mesenchymal cells), and endothelial cell proliferation (embryonic and preexisting).

Model Systems

A number of model systems are useful for the present methods. Examples include the chicken chorioallantoic membrane (CAM) model of vascular development and angiogenic model in nude mice.

One model system for screening compounds that regulate vascular specific genes as described in the present methods includes developing blood vessels in the chorioallantoic membrane of the chicken (CAM). Using this model system, the present inventors identified the chicken homologue of ELF-1 (cELF-1). Surprisingly, the inventors identified a member of the Ets transcription factor family, ELF-1 that is enriched in the developing blood vessels of the chicken embryo.

In this model, blood vessels were dissected out of the CAM at day 5 and blood vessel development plateaus at about day 16. RT-PCR with degenerate oligonucleotides encoding amino acids within the highly conserved DNA binding domain of the Ets factors was used to identify the Ets factors that are expressed in the CAM. A partial cDNA fragment of a chicken Ets factor, CAM-Ets4, with highest homology to ELF-1 and NERF was isolated. The chicken Ets homologue is highly enriched in the developing blood vessels of the CAM compared to fetal chicken liver and brain.

A λgt-10 chicken embryo library was screened and a full-length cDNA fragment encoding CAM-Ets4, including the 5' and 3' untranslated regions was isolated. Sequence analysis demonstrates that the full-length CAM-Ets4 is the chicken homologue of ELF-1. This sequence is set forth in FIG. 1 (SEQ ID NO. 2).

The ability of cELF-1 to function as a transcription factor was tested by examining the ability of cELF-1 to transactivate the Tie2 promoter. cELF-1 can transactivate the Tie2 promoter. We have previously shown that human ELF-1 can transactivate the Tie2 promoter via Ets binding sites.

Two dominant negative forms of cELF-1 block cELF-1 function. The two dominant negatives of cELF-1 included one which contained only the Ets domain with an in frame optimal ATG at the 5' end (DN1), and a second that contained the entire transactivation domain but lacked the DNA binding domain (DN2). Both of these mutant forms of cELF-1 blocked transactivation of the Tie2 promoter by cELF-1 by over 90%. To more carefully examine cELF expression during blood vessel development, in situ hybridization was performed in the chicken CAM. Surprisingly, cELF-1 expression is enriched in the chicken CAM blood vessels. Expression is particularly prominent in the smaller branching vessels. As shown below, minimal staining is seen in the sense control.

These results demonstrate that cELF-1 is a strong transactivator of the Tie1 and Tie2 genes, can bind to specific Ets sites within the Tie1 and Tie2 promoters and is enriched in developing blood vessels. Thus, this transcription factor contributes to the transcriptional regulation of vascular development. This result was surprising because ELF-1 was originally described as a regulator of T-cell specific genes including the Interleukin-2(IL-2) gene, IL-2 receptor, GM-CSF, and CD4 genes (Serdobova I, et al. J Exp Med. 1997;185:1211–1221; Thompson C B, et al. Mol Cell Biol. 1992;12:1043–1053; Wang C Y, et al. Mol Cell Biol. 1994;14:1153–1159). In addition we and others have recently shown that ELF-1 is also expressed in B cells where it regulates IgH gene expression (Akbarali Y, et al. J Biol Chem. 1996;271:26007–26012). This, however, is the first report to demonstrate a role for ELF-1 in vascular-specific gene expression during blood vessel development in addition to its role in regulating genes of hematopoietic origin. See Dube, A., et al., "ELF-1 is a transcriptional regulator of the Tie2 gene during vascular development," Circ. Research, 2000, in press.

A novel member of the Ets gene family, NERF, was previously isolated and shares the highest degree of homology to ELF-1. NERF and ELF-1 are also involved in the regulation of the B-cell specific tyrosine kinase blk (Oettgen P, et al. Mol Cell Biol. 1996;16:5091–5106). The nucleic acid sequence and amino acid sequence of NERF (including NERF-1 and NERF-2) are described in U.S. Pat. No. 5,721,113, incorporated herein in its entirety.

The chicken homologue of the human Ets factor NERF2, cNERF2 has been isolated and characterized. Northern blot analysis and in situ hybridization demonstrate that cNERF2 is enriched in the developing blood vessels of the chicken CAM. cNERF2 functions as a competitive inhibitor of cELF-1. Although in vitro translated cELF-1 and cNERF2 can bind equally well to conserved Ets binding sites in the promoters of the Tie1 and Tie2 genes, cELF-1 preferentially binds to the Ets sites in these promoters during chicken blood vessel development. (John Gaspar, Shelley Thai, Carole Voland, Antoinise Dube, Towia A. Libermann, M. Luisa Iruela-Arispe, and Peter Oettgen, "Opposing Functions of the Ets Factors NERF and ELF-1 in the regulation of the Tie1 and Tie2 genes during Chicken Blood Vessel Development" (in press)).

Other model systems are known to one of ordinary skill in the art can be readily selected and used in accordance with the teachings herein.

Vascular Specific Genes

The methods of the present invention are useful for modulating the activity of vascular specific genes, which control blood vessel development. Conserved Ets binding sites have been identified in the promoters of many vascular specific genes, including the Tie1, Tie2, and Flt-1 genes, and some of these sites have also been shown to be functionally important, as in the Flt-1 gene. Thus, examples of genes which are modulated by the methods of the present invention include genes that have these conserved Ets binding sites, e.g., the Tie1, Tie2, FLK-1 and Flt-1 genes.

Figure 9:
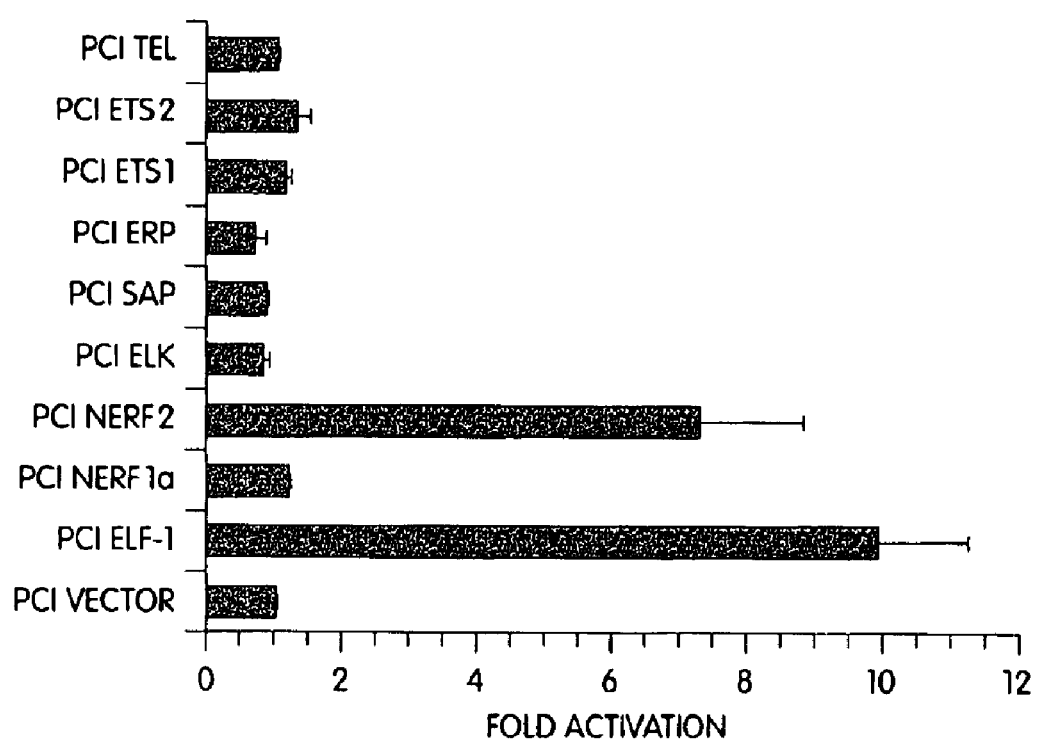
FIG. 9 shows transactivation of the Tie2 promoter/enhancer by selected Ets factors.
Figure 10:
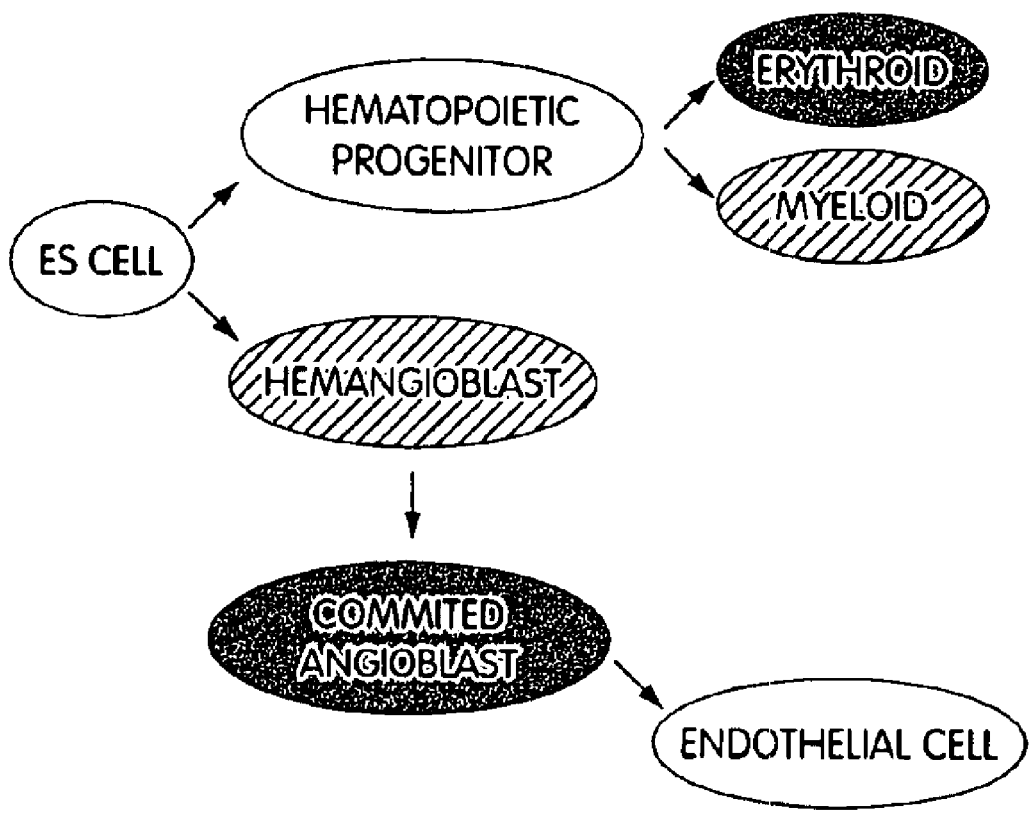
FIG. 10 shows diagrammatically, embryonic stem cell differentiation.

The genomic regulatory regions which are required for vascular specific expression of the Tie2 gene have been characterized. See e.g., Schlaeger, T. M., et al., Proc. Natl. Acad. Sci., USA, 1997; 94:3058–3063. We first compared the ability of several members of the Ets family to transactivate a Tie2 reporter construct containing the promoter and intronic region, up to an intronic enhancer, in HEK 293 cells. As is shown in FIG. 9, two members of the Ets gene family, which are structurally similar, ELF-1 and NERF2, were able to transactivate these regulatory elements of the Tie2 gene up to ten fold, compared to the empty PCI expression vector. In contrast, the other Ets factors tested, including Ets1, Ets2, SAP-1, Elk-1, Tel, and ERP had little or no ability to transactivate the Tie2 gene, despite the ability of many of them to act as strong transactivators in cotransfections of other promoters in the same cells.

The fact that ELF-1 can transactivate the Tie1 and Tie2 genes demonstrates that these genes are targets for ELF-1. The regulatory elements of both the Tie1 and Tie2 genes have been used to direct LacZ gene expression in a vascular-specific manner. Mutations in selected Ets sites in the regulatory regions of the Tie1 and Tie2 genes result in marked reductions in vascular specific gene expression in vivo. Furthermore, with certain mutations, in addition to a reduction in overall vascular-specific gene expression, the LacZ directed gene expression is reduced more in certain vascular beds more than in others (Iljin K, et al. Faseb J. 1999; 13:377–386). Thus, certain Ets factors may be more important for the regulation of vascular-specific gene expression in certain vascular beds. With regard to expression of human and chicken ELF-1, for example, both are expressed only briefly in the fetal brain and not at all in adult brain, whereas both are strongly expressed in the fetal and adult heart supporting a role for ELF-1 for differential gene expression in different tissues. A recent study performed on the transcriptional regulation of the human endothelial nitric oxide synthase(eNOS) gene provides further support that ELF-1 is involved in vascular-specific gene expression. In this study ELF-1 was shown to cooperate with the transcription factors Sp1, Sp3, and MAZ, to form a multiprotein complex required for transcriptional activation of the eNOS gene (Karantzoulis-Fegaras F, et al. J Biol. Chem. 1999;274:3076–3093).

In contrast to ELF-1, Ets-1 has previously been shown to be expressed in developing blood vessels and tumor angiogenesis, but it does not appear to be able to transactivate the core regulatory elements of the Tie2 gene (Kola I, et al. Proc Natl Acad Sci USA. 1993;90:7588–7592; Wernert N, et al. Am J Pathol. 1992; 140:119–127).

The methods of the present invention utilize the role of transcription factors, e.g., ELF-1, in hematopoiesis and vascular development, and in particular in regulating the gene expression of the Tie2 gene. For example, the methods of the present invention are useful for targeting all aspects of blood vessel development, from early endothelial cell differentiation to angiogenesis. For example, as described herein, the methods of the present invention are useful for modulating (i.e., increasing or decreasing) the development of endothelial cells into blood vessels, through vasculogenesis or angiogenesis. However, the methods of the present invention are also useful for a therapeutic role in modulating endothelial cell differentiation. For example, circulating stem cells, which are capable of differentiating into endothelial cells can migrate into regions of the body where angiogenesis then occurs. However, if differentiation into endothelial cells is blocked, angiogenesis will be prevented. Similarly, angiogenesis can be increased by increasing the differentiation of these migrating stem cells into endothelial cells. Thus, the methods of the present invention, which modulate the activity of transcription factors to either increase or decrease endothelial differentiation, can be utilized to control angiogenesis via stem cell differentiation. Such methods can be administered e.g., via viruses that would selectively attach to stem cells or by using small molecules to target these cells. A marker of early differentiation, e.g., CD34, can also be used to target hematopoetic/endothelial cells, and then target TIE1, TIE2, FLK-1 or FLT-1. Thus, the methods of the present invention could be used to block the transcription factors, e.g., NERF-2 or ELF-1 and inhibit endothelial cell differentiation.

Methods of Treating Diseases:

The methods of the present invention for modulating blood vessel development in a mammal comprise altering or modulating the activity of a transcription factor expressed in the cells of a tissue, organ or synovial fluid of the mammal. The term altering or modulating as defined above includes both up-regulation (i.e., turning on or increasing) and down regulation (i.e., turning off or decreasing) expression or activity of the transcription factor.

Thus, decreasing the activity of a transcription factor includes either decreasing, i.e., down-regulating, the activity of the transcription factor or down regulating, including blocking, the expression of the transcription factor. Methods of down-regulating expression of the transcription factor can be accomplished in many ways that are known to one of ordinary skill in the art, e.g., inhibiting the activation of the promoter for the gene encoding the transcription factor, using dominant negative mutants, antisense RNAs, and DNA viruses.

Methods of down-regulating activity of the transcription factor include adding inhibitors that prevent binding of the transcription factor to its target genes prevent interaction of ELF-1 with other proteins, prevent phosphorylation or acetylation of ELF-1, prevent nuclear translocation of ELF-1. Examples of such inhibitors include small molecules, ELF-1 polypeptide antagonists, antibodies that bind to ELF-1 binding regions and other substances that can be selected by one of ordinary skill in the art based on their knowledge and the teachings herein.

In certain diseases, treatment may require up-regulating the activity of the transcription factor, expression of the transcription factor and/or the amount of the transcription factor. For example, in certain diseases, it may be found that it is desirable to induce ELF-1 to increase the expression of certain genes. Thus, it would be desirable to increase expression of ELF-1, the activity and/or the amount of the ELF-1 polypeptide to treat diseases associated with decreased blood vessel development or when it is desirable to increase blood vessel development above the normal development. For example, in certain diseases it is desirable to increase blood flow to an area, e.g., in cases of stroke, heart attack, coronary heart disease, ischemia, poor circulation, peripheral vascular disease or cerebral vascular disease. Thus, it would be useful to increase ELF-1 production or activity in a localized area, which in turn would increase vascularization in that area, e.g., in cases of stroke.

In other diseases, treatment may require down-regulating the activity of the transcription factor, expression of the transcription factor and/or the amount of the transcription factor. For example, in certain diseases, it may be found that it is desirable to reduce the activity of ELF-1 to decrease the expression of genes associated with blood vessel development. Thus, it would be desirable to decrease the expression, activity and/or the amount of the ELF-1 polypeptide to treat diseases associated with increased blood vessel development, or when it is desirable to decrease blood vessel development below the normal development. For example, in certain diseases it is desirable to decrease blood flow to an area, e.g., cancer, diabetic retinopathy, inflammation in joints of patients with rheumatoid arthritis, localized inflammation, psoriasis, or inflammatory bowel disease. In cancer, decreasing ELF-1 may lead to decreased angiogenic responses that destroy the cancer.

In other methods of treating diseases, the expression of vascular specific gene is altered by modulating the expression of a transcription factor, which affects the expression of the gene. Examples of vascular specific genes include, but are not limited to, Tie1 gene, Tie2 gene, FLK-1 gene or FLT-1 gene.

In some embodiments, the expression of the vascular specific gene is decreased by decreasing the expression or the activity of the transcription factor. Methods of decreasing the activity of the transcription factor are known in the art and include, e.g., decreasing the function of the transcription factor or blocking the expression of the transcription factor. In other embodiments, altering the expression of the vascular specific gene involves increasing the activity of the transcription factor. The activity of a transcription factor can be increased by methods known in the art, e.g., either increasing the function of the transcription factor or increasing the expression of the transcription factor.

Examples of diseases which can be treated by increasing blood vessel development include, but are not limited to, coronary heart disease, ischemia, poor circulation, peripheral vascular disease or cerebral vascular disease In the methods in which the activity of the transcription factor is increased, this can be accomplished in many ways that are known to one of ordinary skill in the art, e.g., activating the promoter for the gene encoding the transcription factor. In certain embodiments, the step of increasing activation further comprises providing a substance (agonist) that increases the function or expression of the transcription factor. The substance can be selected by one of ordinary skill in the art but include, small molecules, and peptides. Examples of such substances include, e.g., proangiogenic compounds such as growth factors such as bFGF, VEGF, and EGF. Preferred substances mimic or enhance the activity of the transcription factor.

In certain methods, the transcription factor comprises ELF-1 and the step of inhibiting activation further comprises preventing the binding of binding proteins to the ELF-1 promoter. The step of preventing binding may comprise the step of mutating the ELF-1 promoter or otherwise blocking the binding site.

The substance that alters the activity of the transcription factor can be provided in vivo systemically, or alternatively, the substance is provided to the site of disease, e.g., heart muscle, arthritic joints, etc., depending on the result desired. For example, the substance, e.g., small molecule drugs, peptides, dominant negative mutants by gene delivery mechanisms, antisense RNA, can be used to block the function or expression of the transcription factor, e.g., ELF-1, systemically to treat a disease such as rheumatoid arthritis. Alternatively, local delivery of an ELF-1 blocking agent can be used to treat localized inflammation as is seen in the joints of rheumatoid arthritis patients, or alternatively, an agonist can be delivered to heart muscle to increase EFL-1 transcription, and therefore, angiogenesis.

The methods of the present invention also provide a novel method of modulating angiogenesis by altering the differentiation of circulating stem cells into endothelial cells after modulating the expression of these factors in stem cells. Thus, the transcription factors can be used to either increase, or decrease, differentiation of circulating stem cells, to either increase or decrease angiogenesis.

The methods of the present invention can be used to modulate the development of endothelial cells from undifferentiated stem cell to fully committed endothelial cell. The methods can also be used for either disrupting, or promoting, interactions between endothelial cells and surrounding cells, which is essential for blood vessel development. For example, The methods of the present invention can be used to block Tie receptors by inhibiting the interaction of endothelial cells with mesenchymal cells or smooth muscle cells. In addition, as further described herein, the methods of the present invention can be used to modulate the proliferation of preexisting endothelial cells, i.e., angiogenesis.

The methods described herein for modulating blood vessel development and/or endothelial cell differentiation by modulating the activity of certain transcription factors can be sued as therapy for certain diseases either alone or in conjunction with other therapies. For example, other transcription factors, e.g., other GATA factors or SCL transcription factor can be modulated. Or, alternatively a combination of blocking more than one transcription factor will result in a more robust therapy for blocking TIE1, TIE 2, FLK or FLT gene expression.

Methods of Screening for Agonist and Antagonist Compounds

As shown herein, up-regulation of ELF-1 turns on, i.e., transactivates, genes under ELF-1 control and down-regulation of ELF-1 will turn off genes under ELF-1 control.

Transcription factors such as ELF-1 function by activating or repressing genes that they regulate. As aforesaid, ELF-1 controls a number of genes involved in blood vessel development. Also as aforesaid, modulation of this function is useful in developing therapeutics to control certain disease conditions. Thus, one embodiment of the invention provides for screening for compounds that modulate ELF-1 expression or ELF-1 polypeptide activity. The term modulate includes both up-regulation (i.e., turning on or increasing) and down regulation (i.e., turning off or decreasing) expression or activity. Thus, ELF-1 may be employed in a screening process for compounds which activate (agonists) or inhibit activation (antagonists) of this transcription factor and/or the genes that it regulates.

Certain methods involve contacting a cell or an isolated system (e.g., a solution) containing ELF-1 gene or polypeptide with the agent that is to be screened for ELF-1 modulatory activity and detecting the binding of that agent to the gene or polypeptide. Methods of assaying for binding interactions are well known to those of ordinary skill in the art.

Compounds that bind to ELF-1 nucleic acid or polypeptide are expected to provide lead compounds for therapeutic evaluation and/or development.

The invention provides methods of screening compounds that are capable of reducing blood vessel development (i.e., ELF-1 antagonists). One such method involves the use of cells, which do not normally express a measurable transcription factor but do express the transcription factor in the presence of a pro-angiogenic agent. In this method a portion of the cells are contacted with a compound to be screened and another portion of the cells is used as a control without the compound. A proangiogenic agent is also added to the cells and the expression of the transcription factor in the cells is measured. The amount of expression of the transcription factor in the cells containing the compound is compared with the control portion of cells. Methods of measuring the expression of the transcription factor are known in the art and are examples are described herein. In one example of such screening methods, the transcription factor is an Ets transcription factor, preferably ESE-1. However, the use of other transcription factors is envisioned as well.

Pro-angiogenic substances are known in the art. Examples of proangiogenic substances include, but are not limited to, growth factors, e.g., bFGF, VEGF, EGF and HGF and IL-8.

Examples of cells which are useful in screening methods of the present invention include, but are not limited to, endothelial cells, such as HUVECs, HAEC, as well as endothelial cells at any stage of differentiation, from stem cell to fully differentiated endothelial cell.

Another method uses cells which do not normally express the transcription factor of interest, e.g., ELF-1, but are transfected to express the transcription factor. Such transfection methods are known in the art. Useful cells include cells from mammals, yeast, *Drosophila* or *E. coli*. In particular, a polynucleotide encoding ELF-1 is employed to transfect cells that do not normally express ELF-1 to thereby express the ELF-1. Cells expressing the polypeptide are then contacted with a test compound to observe binding, stimulation or inhibition of a functional response. In one embodiment, this technique is employed to screen for compounds which decreases activation of ELF-1 by contacting the cells which encode the polypeptide with a molecule that binds ELF-1, a proangiogenic agent and a compound to be screened. Inhibition of the signal generated by the ELF-1 binding molecule indicates that a compound is a potential antagonist for the ELF-1, i.e., inhibits activation of the polypeptide. The technique may also be employed for screening of compounds which activate the polypeptide by contacting such cells with compounds to be screened and determining whether such compound generates a signal, i.e., activates the polypeptide.

In another method cells are transfected with an ELF-1 response reporter construct and the response to proangiogenic compound is measured in the absence or presence of the test compound.

Similar methods can also be used for screening for compounds that up-regulate (e.g., a pro-angiogenic agent) or down regulate (e.g., an ELF-1 repressor agent) the expression or activity of the transcription factor and therefore modulate blood vessel development response. For example, in one such method to screen for pro-angiogenic agents, cells that do not normally express the transcription factor are used. A portion of the cells are contacted with a compound to be screened for increased ELF-1 expression and another portion of the cells is used as a control without the compound. Expression of the transcription factor in the cells is measured. The amount of expression of the transcription factor in the cells containing the compound is compared with the control portion of cells. If the expression increases in the presence of the compound, it is a proangiogenic agent. This agent can then be retested, if desired, in the previous methods in order to find compounds that prevent inflammation caused by this agent. Or this agent can be used when it is desirable to increase ELF-1 expression, e.g., to increase blood vessel development.

The compounds of to be tested include small molecules, peptides, antisense RNA or viral DNA. Examples of potential ELF-1 polypeptide antagonists include antibodies or, in some cases, oligonucleotides which bind to the polypeptide but do not elicit a response, e.g., angiogenic response, such that the activity of the polypeptide is prevented.

Potential antagonists also include proteins which are closely related to ELF-1, i.e. a fragment of ELF-1, or a mutated ELF-1 which have lost biological function or acts as a dominant negative and, when binding to ELF-1 target genes or to ELF-1 interacting proteins, elicit no response or compete with wild type ELF-1.

A potential antagonist also includes an antisense construct prepared through the use of antisense technology. ELF-1 gene regulation can be downregulated or entirely inhibited by the use of antisense molecules. An "antisense sequence" or "antisense nucleic acid" is a nucleic acid is complementary to the coding ELF-1 mRNA nucleic acid sequence or a subsequence thereof.

Binding of the antisense molecule to the ELF-1 mRNA interferes with normal translation of the ELF-1 polypeptide. Examples of antisense molecules that can be used in the present invention include oligonucleotides and oligonucleotide analogs that are hybridizable with ELF-1 messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of ELF-1 polypeptides.

Another potential antagonist is a small molecule which binds to the ELF-1 polypeptide, making it inaccessible to bind to DNA or other proteins that are critical for its function as a transcription factor such that normal biological activity is prevented. Examples of small molecules include, but are not limited to, small peptides or peptide-like molecules, and non-peptide molecules.

A mutated version of an ELf-1 construct can act as a "dominant-negative" transcription factor to silence ELF-1 regulated genes. Using the information provided herein ELF-1 polypeptide variants can be routinely produced. Methods of making other such polypeptide variants or muteins are well known to those of skill. Screening of such polypeptides (e.g., in DNA binding assays or for competitive inhibition of full-length normal ELF-1 polypeptides) can be accomplished with only routine experimentation. Using high-throughput methods, as described herein, literally thousands of agents can be screened in only a day or two.

Alternatively, antagonists or agonists of the present invention may comprise molecules which activate or repress genes regulated by this transcription factor. Electrophoretic mobility shift assays where ELF-1 binding sites in promoters are used together with ELF-1 recombinant proteins can be used to identify genes regulated by ELF-1. Modulation of the expression of these genes by test compounds to identify potential antagonists and agonist can then be performed in accordance with the above-described methods.

New chemical entities with useful properties are generated by identifying a chemical compound (called a "lead compound") with some desirable property or activity, creating variants of the lead compound, and evaluating the property and activity of those variant compounds. High throughput screening methods are replacing conventional lead compound identification methods because they enable quick and efficient testing of large numbers of compounds. In one example of a high throughput screening method, a library containing a large number of potential therapeutic compounds (candidate compounds) is used. These are termed "combinatorial chemical libraries" and can be screened using any of the methods described herein. The compounds thus identified can serve as conventional "lead compounds" or can themselves be used as potential or actual therapeutics. Preparation and screening of combinatorial chemical libraries is well known to those of skill in the art.

High throughput assays for the presence, absence, or quantification of particular nucleic acids or protein products are well known to those of skill in the art. Similarly, binding assays and reporter gene assays are similarly well known, as are high throughput screening methods for proteins, high throughput screening methods for nucleic acid binding (i.e., in arrays), and methods of screening for ligand/antibody binding. In addition, high throughput screening systems are commercially available Any of the assays for compounds modulating ELF-1 gene expression and/or ELF-1 protein activity described herein are amenable to high throughput screening. Preferred assays thus detect enhancement or inhibition of ELF-1 gene transcription, inhibition or enhancement of ELF-1 polypeptide expression, inhibition or enhancement of DNA binding by ELF-1 polypeptide inhibition or enhancement of protein interaction with ESE-1, inhibition or enhancement of ELF-1 phosphorylation or aceylation, inhibition or enhancement of ELF-1 nuclear 1 cytoplasmic translocation, or inhibition or enhancement of expression of native genes (or reporter genes) under control of the ELF-1 polypeptide.

Antagonists for ELF-1 may be employed for a variety of therapeutic and prophylactic purposes for such diseases or disorders as described herein.

Methods of Diagnosing Disease and Monitoring Treatment

The invention also relates to methods of diagnosing the presence of a disease that increases blood vessel development, e.g., angiogenesis, in a mammal. In one example of such a method, a sample of blood, tissue, synovial fluids urine or CSF or organ is removed from the mammal. The presence and/or amount of a transcription factor of interest, e.g., ELF-1 is then measured using methods known in the art, and described herein. The sample tested does not normally express the transcription factor of interest in detectable amounts in the absence of the inflammatory disease.

Examples of diseases which can be diagnosed include, but are not limited to, cancer, inflammation, diabetic retinopathy, inflammation in joints of patients with rheumatoid arthritis, localized inflammation, psoriasis and inflammatory bowel disease.

Similarly, the invention also provides methods of monitoring the treatment of a disease. In one such methods, a sample is removed from the mammal subsequent to treatment and the presence or amount of a transcription factor is measured. Again, the transcription factor is not present in the sample in detectable amounts in the absence of the disease. As above, the sample can be tissue, synovial fluid, blood, urine, CSF or an organ sample. This procedure can be repeated at subsequent intervals and the amounts of the transcription factor compared in order to monitor the effectiveness of the treatment over time.

Pharmaceutical Compositions

The present invention also relates to pharmaceutical compositions for the treatment of angiogenesis, vasculogenesis or endothelial differentiation comprising a compound that alters or modulates the expression of a transcription factor and a pharmaceutically acceptable carrier. Preferred compositions comprise compounds that alter the expression or function of ELF-1. Examples of compounds that are useful in such compositions include small molecules, peptide, or antisense RNA. In certain embodiments, the composition further comprises other agents that are known to be useful treatments.

By pharmaceutically acceptable carrier, it is meant to include, but is not limited to, saline, buffered saline, dextrose, water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration of Compounds

Polypeptides and other compounds of the present invention may be employed alone or in conjunction with other compounds, such as therapeutic compounds.

The ELF-1 polypeptides, anti-ELF-1 antibodies, or other ELF-1 modulators of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the ELF-1 polypeptides and related compounds described of, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for localized administration to areas of angiogenesis, vasculogenesis or endothelial differentiation, in particular, joints or inflamed tissues. In another embodiment, the compositions are useful for parenteral administration, such as intravenous administration or administration into a body cavity or lumen of an organ. The compositions for administration will commonly comprise a solution of the ELF-1 polypeptide, antibody, or agonist or antagonist dissolved in a pharmaceutically acceptable carrier, preferably an aqueous carrier. A variety of aqueous carriers can be used, e.g., buffered saline and the like. These solutions are sterile and generally free of undesirable matter.

These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compounds in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art.

The compositions containing the present ELF-1 polypeptides, antibodies or antibody, antagonists, or agonists, or a cocktail thereof (i.e., with other proteins), can be administered for therapeutic treatments. To treat diseases characterized by over expression of ELF-1, one can administer an anti-ELF-1 antibody or an abnormal ELF-1 protein that is not biologically active. Such inactive ELF-1 polypeptides can, for example, interfere with binding of native ELF-1 polypeptide to its DNA binding site, or to RNA polymerase or other protein through which the ELF-1 transcription factor activity is mediated. Alternatively, when it is desirable to increase ELF-1 activity compounds can be added to either promote ELF-1 expression or activity, or even just add ELF-1 to the site to increase the amount available.

In therapeutic applications, compositions are administered to a patient suffering from a disease (e.g., coronary heart disease) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of interest to effectively treat the patient. Among various uses of the ELF-1 polypeptides, polypeptide subsequences, anti-ELF-1 antibodies and small molecules, and are treatment a variety of inflammatory disease conditions, including rheumatoid arthritis, vascular inflammation, etc., as described above.

Gene Therapy

The ELF-1 polynucleotides, polypeptides, agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well known in the art and their use in the present invention will be apparent from the teachings herein.

Similarly, cells may be engineered in vivo for expression of a polypeptide in vivo by procedures known in the art. For example, a polynucleotide may be engineered for expression in a replication defective retroviral vector. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Such vectors will include one or more promoters for expressing the polypeptide. The selection of a suitable promoter will be apparent to those skilled in the art from the teachings contained herein.

Adenoviral vectors can be used for gene therapy according to known methods in the art, including the following: Muruve D, Manfro R C, Strom T B, and Libermann T A. Ex vivo adenovirus-mediated gene delivery leads to long-term expression in pancreatic islet transplants. Transplantation; 1997; 64: 542–546; Muruve D A, Nicholson A G, Manfro R C, Strom T B, Sukhatme V P, and Libermann T A. Adenovirus mediated expression of FAS ligand induces hepatic apoptosis after systemic administration and apoptosis of ex vivo infected pancreatic islet allografts and isografts. Human Gene Ther.; 1997; 8: 953–965 and Sata M, Perlman H, Muruve D A, Silver M, Ikebe M, Libermann T A, Oettgen P, and Walsh K. Fas ligand gene transfer to the vessel wall inhibits neointima formation and overrides the adenovirus-mediated T cell response. 1998: Proc. Natl. Acad. Sci. USA; 95: 1213–1217.

A variety of adenoviral vectors have been generated which have been used in various in vivo gene therapy settings (Muruve D, M. R. C., et al., 1997. Transplantation 64:542–546; Muruve, D. A., et al., 1999. Hum Gene Ther 10:965–76; Muruve D A, N. A., et al., 1997. Human Gene Ther. 8:953–965; Sata M, P. H., et al., 1998. Proc. Natl. Acad. Sci. USA 95:1213–1217). We have used replication deficient adenovirus type 5, one of the most efficient vectors for transducing non-replicating and replicating eukaryotic cells, to transfer genes into murine pancreatic islets in an allogeneic organ transplant model as a tool to prevent allograft rejection. We have demonstrated that we can achieve long term gene expression in pancreatic islet transplants using adenovirus-mediated gene delivery. We also demonstrated that adenovirus mediated expression of FAS ligand induces hepatic apoptosis after systemic administration and apoptosis of ex vivo infected pancreatic islet allografts and isografts. We have used Fas ligand gene transfer to the vessel wall to inhibit restenosis after balloon angioplasty.

The present invention is further illustrated by the following Examples. The Examples are provided to aid in the understanding of the invention and are not construed as a limitation thereof.

Certain terms used herein are explained in the foregoing glossary. All examples are carried out using standard techniques, which are well known and routine to those of skill in the art, except where otherwise described in detail. Routine molecular biology techniques of the following examples can be carried out as described in standard laboratory manuals.

EXAMPLES

Materials and Methods for Examples 1–8

Cell Culture

Human umbilical vein endothelial cells (HUVECs), Human dermal microvascular endothelial cells, and human aortic endothelial cells (HAECs) were obtained from Clonetics. PY41 endothelial cells were a generous gift from Vicki Bautch (Dubois-Stringfellow N, et al. Am J Pathol. 1994;144:796806). The murine yolk sac endothelial cell line(C166) and the EOMA cells were a generous gift from Robert Auerbach, and were grown as previously described (Lu L S, et al. Proc Natl Acad Sci USA. 1996;93:14782–14787; Obeso J, et al. Lab Invest. 1990;63:259–269).

RNA Extraction and Northern Blot Analysis.

Total RNA was extracted from CAM blood vessels, cultured CAM endothelial cells, and blood derived from the CAM at different developmental stages as previously described (Chomczynski P, Sacchi N. Anal Biochem. 1987; 162:156–159). Total RNA was electrophoresed and transferred onto a nytran membrane. The filters were blocked in prehybridization solution and then hybridized with a cELF-1 specific probe. The cELF-1 cDNA fragment used to generate the probe is 700 bp in length and encodes the first 100 amino acids of the cELF-1 protein and 100 bp of the 5' untranslated region. The size of the band detected by Northern blot analysis is 3.4 Kb. To normalize for loading and transfer efficiency, the membranes were rehybridized with a probe for the 36B4 chicken housekeeping gene. The size of the band detected by Northern blot analysis is 1.0 Kb.

RT-PCR and Chicken λ-Phage Library Screen

To identify Ets factors which are expressed in the developing blood vessels of the chicken CAM, RT-PCR was performed using RNA extracted from the CAM blood vessels. cDNA was generated from 2 ug of total RNA by using random hexamer priming. Degenerate oligonucleotides corresponding to conserved regions within the Ets DNA binding domain were use as previously described (Lopez M, et al. Mol Cell Biol. 1994;14:3292–3309). PCR fragments were subcloned and fragments of the expected sized were sequenced. A 5 day chicken yolk sac library(Stratagene) was plated and screened with a partial cDNA fragment for cELF-1. Two full length cDNA clones were isolated. For RT-PCR of the human and mouse endothelial cells, the following ELF-1 specific primers were used which recognize both mouse and human ELF-1; 5'-ATGGCTGCTGTTGTCCAAC-3' (SEQ ID NO: 4) and 5'-CCTGAGTGCTCT(C/T)CCCAT-3' (SEQ ID NO: 5) with an expected amplification product of 700 bp, and the GAPDH primers used were 5'-CAAAGTTGTCATGGATGACC-3' (SEQ ID NO: 6) and 5'-CCATGGAGAAGGCTGGGG-3' (SEQ ID NO: 7) with an expected amplification product of 200 bp. PCR reactions were performed as previously described (Oettgen P, et al. Genomics. 1997;445:456–457).

In Situ Hybridization.

Whole-mount in situ hybridization on E3 chick embryos and E10 CAMs were carried out as described by Wilkinson (Wilkinson D G, et al. Development. 1987;99:493–500). The sense and antisense probes were derived from the same 700 bp fragment that was used for Northern blot analysis that was subcloned into the PCRII vector(Invitrogen) containing both a T7(sense) and an Sp6(antisense) promoter. In brief, embryos were fixed, dehydrated and rehydrated through a methanol series, and washed in 1×PBT (PBS plus 0.1% Tween-20). Embryos were then permeablized at room temperature. After color developed to the appropriate intensity, specimens were washed several times and then rehydrated through the graded methanol baths. Images of the embryos were obtained suspended in 80% glycerol using a 3CCD toshiba camera on a Nikon SMZ-U dissecting microscope. Digoxigenin labeled RNA probes were prepared per the manufacturer's recommendations(Roche). The level of digoxigenin incorporation was assessed by using a dot blot comparison to a standard(Roche).

Immunohistochemistry.

Paraffin embedded E4 and E5.5 chicken embryos were stained with a rabbit polyclonal anti-cELF-1 antibody. Sections were clarified with xylene and rehydrated through a decreasing gradient of EtOH. After several washes with ddH$_2$O and 1×PBS, sections were treated with 0.1 mg/ml proteinase K in 1×PBS. Hybridization with an anti-cELF-1 probe was performed after overnight after blocking for 1 hour with 2% goat serum in 1×PBT (PBS containing 0.05% Tween-20. Sections were then incubated with biotinylated anti-rabbit (Vector Lab) and flourescein avidin DN (Vector Lab), consecutively. Immunostained sections were then analyzed by confocal microscopy. Nuclear staining was made possible with the addition of 0.1 mg/ml propidium iodine dissolved in 1:1 PBS/glycerol mounting medium.

DNA Transfection Assays.

Cotransfections of 1.5–2×10$^5$ endothelial cells or 293 HEK cells were performed using 1.75 ug of the reporter gene construct DNA and 0.75 ug of the expression vector DNA with Lipofectamine (Gibco BRL). The cells were harvested 16 hours after transfection and assayed for luciferase. Individual transfections were performed in duplicate and were repeated independently in triplicate with similar results. Cotransfection of a second plasmid for determination of transfection efficiency was omitted because potential artifacts with this technique have been reported (Farr A, Roman A. Nucleic Acids Res. 1992;20:920), and because many commonly used viral promoters contain potential binding sites for Ets factors.

In Vitro Transcription-Translation.

Full length chicken and human ELF-1 cDNA encoding the entire open reading frames were inserted downstream of the T7 promoter into the Bluescript vector. Coupled in vitro transcription-in vitro translation reactions were performed with 1 ug of plasmid DNA using the TNT reticulocyte lysate kit (Promega) and T7 RNA polymerase as recommended by the manufacturer. The plasmid vector without an insert was used as a control.

Electrophoretic Mobility Shift Assay (EMSA).

DNA binding reactions were performed as previously described (Lopez M, et al. Mol Cell Biol. 1994; 14:3292–3309; Libermann T A, et al. Mol Cell Biol. 1990;10:3155–3162). In brief 20 ul samples containing 2 ul of in vitro translated products or cell extracts were incubated with a solution containing $^{32}$P-labeled double stranded probes (30,000 cpm). Samples were incubated in the presence or absence of increasing amounts of cold competitor (5, 50 ng) for 15 to 20 minutes at room temperature and run on a 4% polyacrylamide gel (acrylamide-bisacrylamide, 29:1) containing a buffer of 0.25×TBE (22.5 mM Tris Borate, 0.5 mM EDTA). Oligonucleotides used as probes and for competition studies are as follows:

```
Tie2 promoter oligonucleotide           (SEQ ID NO:8)
5'-TGCAAAGGAAACAGGAAAAAGGAACTTAAC-3'

3'-ACGTTTCCTTTGTCCTTTTTCCTTGAATTG-5'

Tie1 P1                                 (SEQ ID NO:9)
5'-ACTGGCTTCCTCCCTTTCCTGTCTC-3'

3'-TGACCGAAGGAGGGAAAGGACAGAG-5'

Tie1 P2                                 (SEQ ID NO:10)
5'-CCATCATTTCCTCTTCCTCCCCAG-3'

3'-GGTAGTAAAGGAGAAGGAGGGGTC-5'

Tie1 P2 Mut1                            (SEQ ID NO:11)
5'-CCATCATTTAATCTTCCTCCCCAG-3'

3'-GGTAGTAAATTAGAAGGAGGGGTC-5'

Tie1 P2 Mut2                            (SEQ ID NO:12)
5'-CCATCATTTCCTCTTAATCCCCAG-3'

3'-GGTAGTAAAGGAGAATTAGGGGTC-5'

Tie1 P2 Mut1,2                          (SEQ ID NO:13)
5'-CCATCATTTAATCTTAATCCCCAG-3'

3'-GGTAGTAAATTAGAATTAGGGGTC-5'
```

Example 1

Isolation of the Chicken Homologue of ELF-1 (cELF-1)

In an effort to identify transcription factors belonging to the Ets family that are expressed during blood vessel development we chose to examine the highly vascular chicken chorioallantoic membrane. Vessels within the CAM undergo an exponential growth followed by a quiescent phase. Total RNA was extracted from blood vessels that were microdissected from 10 day old CAMs. RT-PCR was performed with degenerate PCR primers corresponding to conserved regions of the Ets domain allowing the identification of a partial DNA sequence for a member of the Ets factor family. This fragment was used to screen a chicken yolk sac cDNA library, and isolate a cDNA clone encoding the full length chicken homologue of ELF-1 (cELF-1). As is shown in FIG. 1, cELF-1 encodes a 617 amino acid long protein with an expected molecular weight of 71.0 kDa. The highest degree of homology to ELF-1 exists in the DNA binding domain (100%), with overall protein sequence homology of 77%. We have previously identified additional regions of homology between ELF-1 and a closely related Ets factor NERF in the transactivation domain. These four domains (A–D) are also highly conserved between human, murine, and chicken ELF-1 (Oettgen P, et al. Mol Cell Biol. 1996;16:5091–5106). To demonstrate that translation of the cELF-1 generates a protein of the expected size we performed in vitro transcription translation with $^{35}$S-methionine. As is shown in FIG. 2, translation of the cELF-1 and human ELF-1 cDNA fragments generated fragments of the expected size.

Example 2

Expression Pattern of cELF-1 in the Chicken CAM

To determine the expression pattern of cELF-1 in the CAM, northern blot analysis was performed using RNA derived from CAM blood vessels at different developmental stages. As is shown in FIG. 3A, cELF-1 is highly expressed in the CAM blood vessels. Because it has previously been shown that ELF-1 is expressed in T and B cells, we examined the expression of cELF-1 in fetal chicken blood at different stages of development. As expected, cELF-1 is also highly expressed in chicken blood(FIG. 3B). To ascertain whether cELF-1 is expressed in the CAM blood vessels devoid of blood, RNA was extracted from CAM blood vessels flushed free of blood and from unflushed CAMs. Although flushing the blood vessels diminishes the expression of cELF-1, there is still significant expression of cELF-1 in the flushed vessels(FIG. 3C). Furthermore, cELF-1 expression is demonstrated in fetal chicken endothelial cells, as compared to chicken fibroblasts, which demonstrated minimal expression of cELF-1.

Example 3

ELF-1 is Expressed in a Subset of Human and Murine Endothelial Cells

Surprisingly, cELF-1 was highly expressed in the CAM blood vessels. We had previously examined ELF-1 expression in human endothelial cells and had not detected it in either human umbilical vein endothelial cells (HUVECs) or human aortic endothelial cells (HAECs) (Dube A, et al. Circ Res. 1999;84:1177–1185). To extend these studies we examined additional murine and human endothelial cells for the expression of ELF-1. As is shown in FIG. 3D, ELF-1 is also expressed in the murine yolk sac endothelial line C166, EOMA and PY41 endothelioma lines, and human dermal microvascular endothelial cells. This suggests that ELF-1 is only expressed in a subset of endothelial cells. As a positive control we used the B cell lines A20 and HAFTL that we have previously shown express ELF-1 (Oettgen P, et al. Mol Cell Biol. 1996;16:5091–5106).

Example 4

Expression Pattern of cELF-1 in the Embryo

Figure 4:
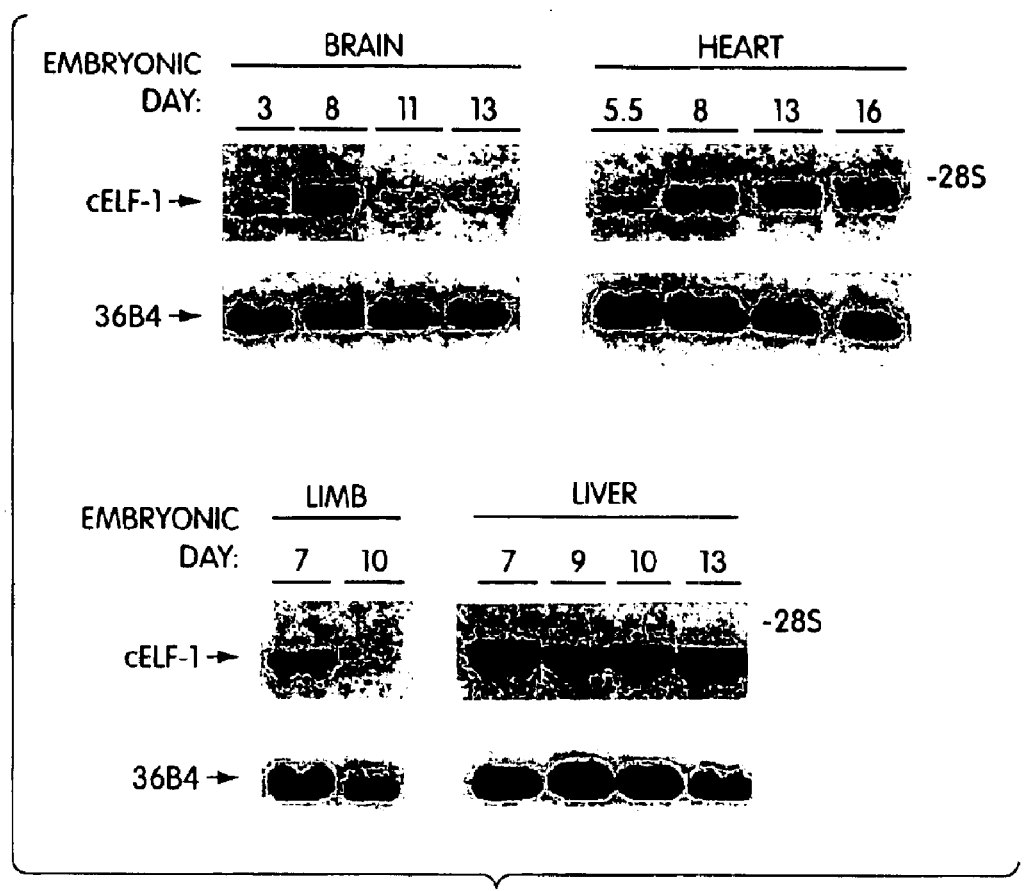
FIG. 4 shows Northern blot analysis of cELF-1 in chicken fetal brain and heart (A) and chicken fetal limb and liver (B). Control is 36B4, a chicken housekeeping gene.

Human ELF-1 is highly expressed in a number of fetal tissues including the heart, liver, and weakly in the brain (Oettgen P, et al. Mol Cell Biol. 1996;16:5091–5106). To ascertain cELF-1 expression at different developmental stages, Northern blot analysis was performed with chicken fetal organs at different developmental stages. As is shown in FIG. 4, cELF-1 is strongly expressed in the fetal liver, in several later developmental stages in the heart, and in a temporal window in embryonic brain and limb development.

Example 5

Figure 5A:
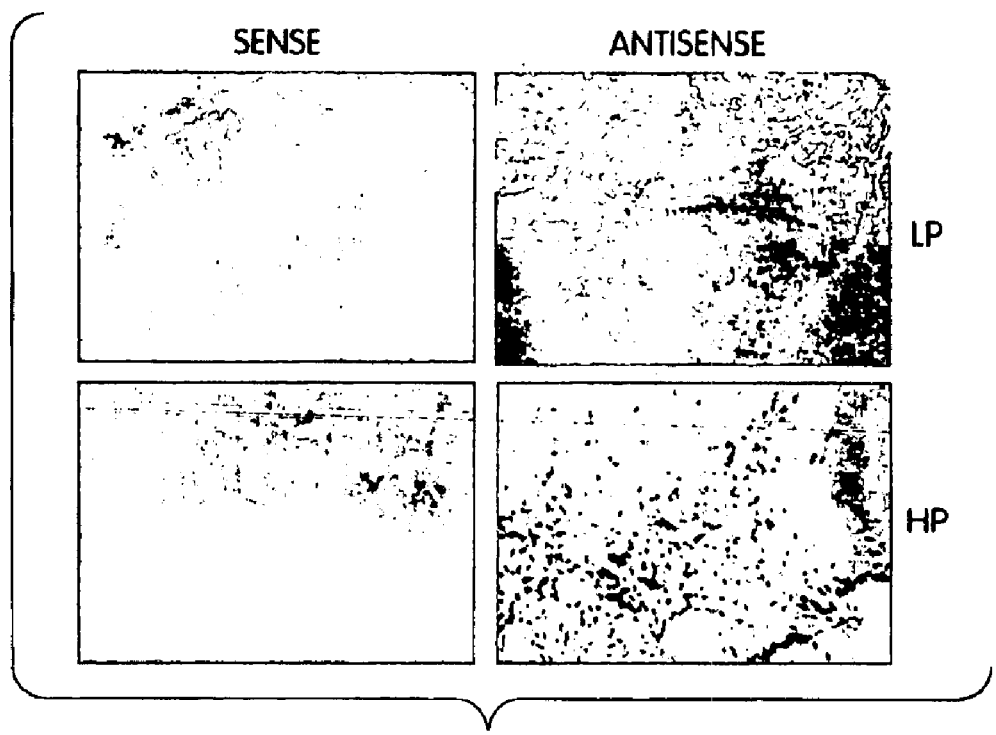
FIGS. 5A and 5B shows whole mount in situ hybridization of cELF-1 in E10 chicken embryos. cELF-1 transcripts were detected along the lining of the larger caliber blood vessels. Note the punctate expression of cELF-1 at a low power(LP) of magnification(10×) in the yolk sac microvessels(Panel A, LP). This expression in the microvessels is seen better at higher power(HP) magnification(40×) (Panel A, HP). cELF-1 is expressed in the chicken fetal heart as early as day 3(Panel B); (red arrow).
Figure 5B:
Figure 6A:
FIGS. 6A–6H shows immunohistochemistry analysis of embryonic days 4 and 5.5 chicken embryos (E4 and E5.5) for expression of cELF-1. Paraffin embedded sections were incubated with anti-cELF-1 and immunocomplexes were detected with biotinylated anti-rabbit anti-body followed by flourescein avidin DN. Visualization of nuclei were performed with propidium iodide.

In Situ Hybridization of cELF-1 in the Developing Blood Vessels of the Chicken CAM Having demonstrated strong expression of cELF-1 in the CAM blood vessels at different stages by Northern blot analysis, the expression of cELF-1 was examined by in situ hybridization, to further define the expression pattern of cELF-1 during blood vessel development. As is shown in FIG. 5A(top panel), cELF-1 is expressed along the lining of the larger caliber blood vessels, with a punctuate expression pattern in the smaller branching vessels. At higher magnification, strong expression of cELF-1 is demonstrated in these smaller caliber branching vessels (FIG. 6A, HP). Whole mount in situ hybridization also confirmed strong expression in the developing heart at day 10(FIG. 5B).

Example 6

Immunohistochemistry of cELF-1 in the Developing Chicken Embryo

Figure 6B:
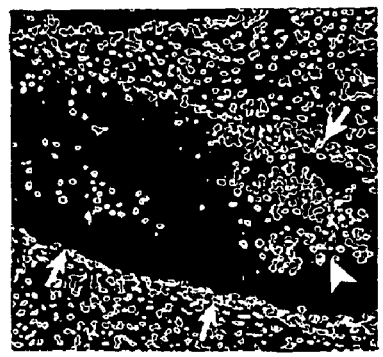
Figure 6C:
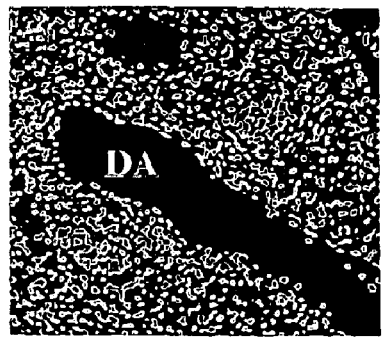
Figure 6D:
Figure 6E:
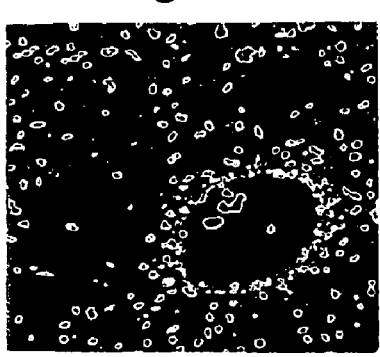
Figure 6F:
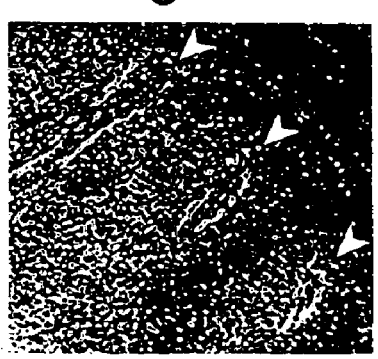
Figure 6G:
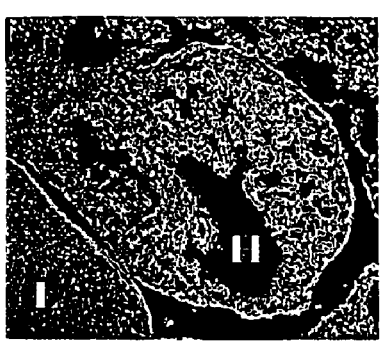
Figure 6H:
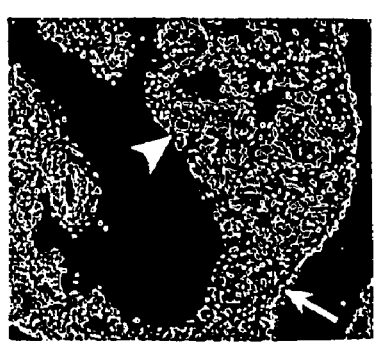

To examine cELF-1 protein expression during chicken embryogenesis, with a particular focus on blood vessel development, immunohistochemistry was performed using an ELF-1 polyclonal antibody. Paraffin embedded sections of embryonic days 4 and 5.5 chicken embryos (E4 and E5.5) were incubated with anti-cELF-1 and immunocomplexes were detected with biotinylated anti-rabbit antibody followed by flourescein avidin DN. Visualization of nuclei was performed with propidium iodide. As is shown in FIG. 6A, cELF-1 is highly expressed in the inner lining of the developing dorsal aorta (DA) of E4 chicken embryos. At higher magnification (FIG. 6B), cELF-1 expression is also appreciated in a subset of blood cells within the lumen of the aorta. No expression could be detected with preimmune serum (FIGS. 6C,D). cELF-1 was also detected in smaller developing chicken blood vessels (FIG. 6E) and in intersomitic vessels of the four day chicken embryo (FIG. 6F). Because we detected high levels of cELF-1 expression in the developing chicken heart by whole mount in situ hybridization, we also examined cELF-1 protein expression in the developing heart. At lower magnification, (FIG. 6G), expression is appreciated in the heart(H) but not the surrounding lung(L). At higher magnification cELF-1 expression is detected in the endocardium of the heart (FIG. 6H). Interestingly, expression was also detected on the pericardial surface.

Example 7 cELF-1 can Transactivate the Tie1 and Tie2 Promoters

Figure 7A:
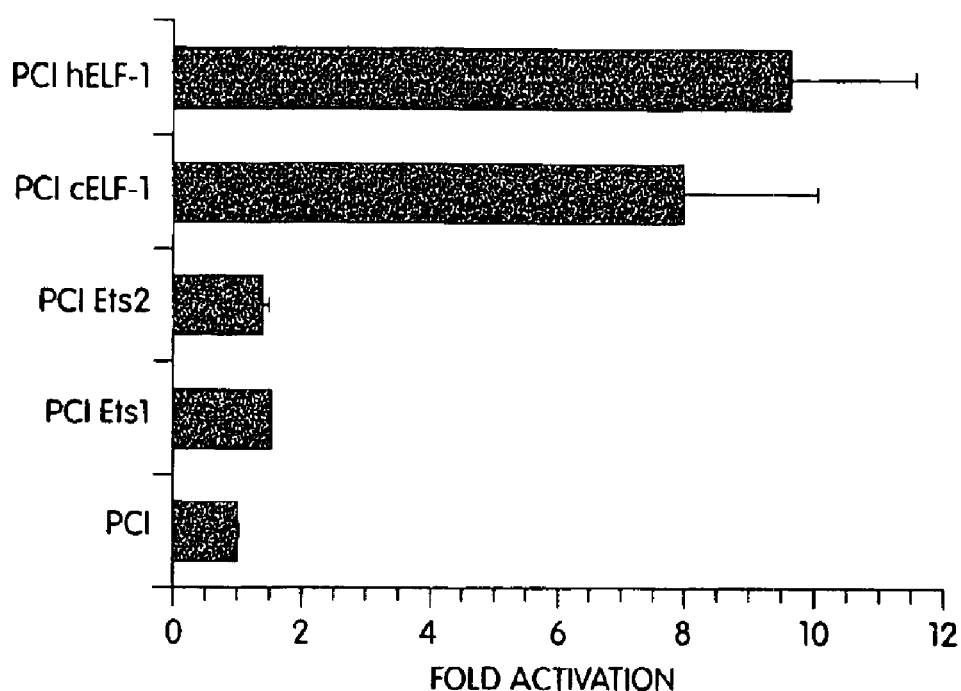
FIGS. 7A and 7B shows a transient cotransfection of Tie2 promoter luciferase reporter construct with PCI expression plasmids for several different Ets factors including cELF-1, ELF-1, Ets-1 and Ets-2 (A), and for the Tie1 promoter luciferase reporter construct (B).
Figure 7B:
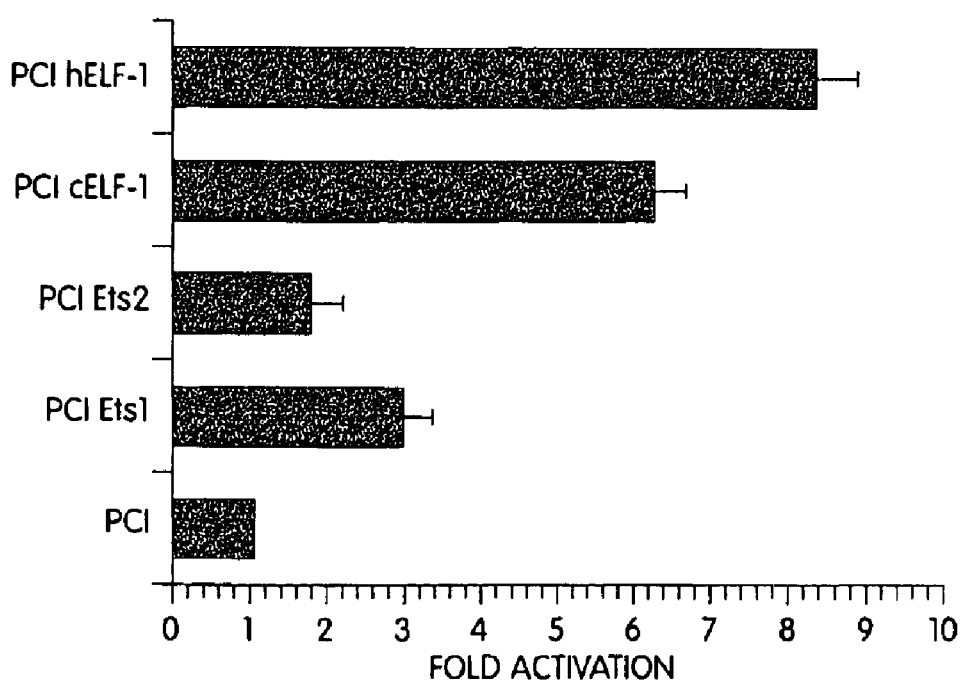

The ability of the chicken and human forms of ELF-1 to transactivate the Tie2 gene promoter was tested. As is shown in FIG. 7A, cELF-1 was similar to human ELF-1 in its ability to transactivate the Tie2 promoter, in contrast to Ets 1 and Ets 2 which only weakly transactivate the Tie2 promoter. We also tested whether the human or chicken ELF-1 could similarly transactivate the Tie1 promoter. As is shown in FIG. 7B, both chicken and human ELF-1 are strong transactivators of the Tie1 promoter. This suggests that both the Tie1 and Tie2 genes may be gene targets for ELF-1.

Example 8 cELF-1 can Bind to Ets Sites in the Tie1 and Tie2 Promoter

The ability of in vitro translated human ELF-1 and cELF-1 to bind to the same Tie2 Ets sites was also examined. As is shown in FIG. 8A, both human and chicken ELF-1 form similar DNA-protein complexes with the Tie2 Ets sites (lane 2 and 3). The ability of an ELF-1 specific antibody to interfere with the formation of these complexes was also tested. This antibody was able to interfere with complex formation of both human and chicken ELF-1. Furthermore the appearance of an additional higher mobility complex when the antibody was used in the presence of cELF-1 suggests the formation of a supershift (see arrow, lane 6). Because several Ets factors may potentially bind to the Tie2 Ets site in vivo in the developing chicken we performed gel shift assays with the Tie2 Ets probe and cell extracts from the chicken CAM. As is shown in FIG. 8B, lane 3, a similar size complex is formed compared to the in vitro translated cELF-1. When the ELF-1 antibody was added, it similarly resulted in the formation of a supershifted complex, suggesting that cELF-1 derived from the chicken CAM is the Ets factor that specifically binds to the Tie2 Ets site.

Figure 8C:
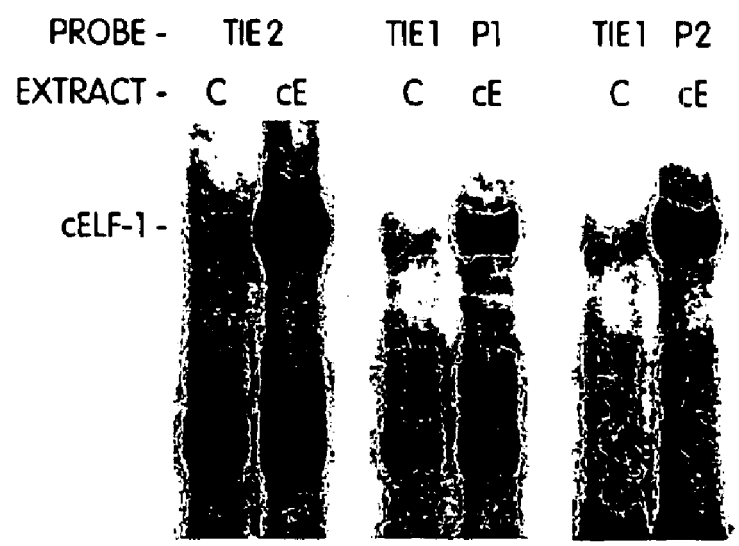
FIG. 8(C) shows EMSA comparing ability of in vitro translated cELF-1(cE) to bind to conserved Ets binding sites in the Tie1 promoter Tie1 P1 and Tie1 P2 compared to the Tie2 probe. Control extracts (C) are used as a negative control.
Figure 8D:
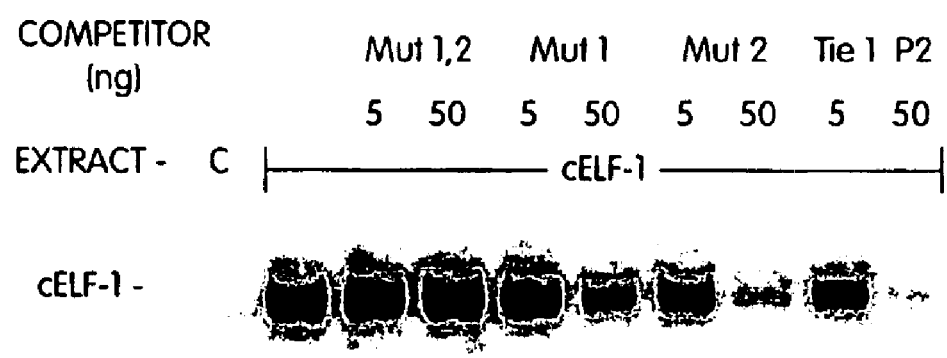
FIG. 8(D) shows competition experiments for binding of cELF-1 to the Tie1 P2 Ets binding sites with 5 or 50 ng of oligonucleotides in which both (Mut1,2), one (Mut1 or Mut2), or none (wild type Tie1 P2) of the Ets sites have been mutated. (See Methods for sequence of the oligonucleotides).

The ability of cELF-1 to bind to conserved Ets sites in the Tie1 promoter was examined. There are two Ets site doublets, P1 and P2 that are highly conserved in this promoter. The ability of cELF-1 to bind to these Ets sites was tested. As is shown in FIG. 8C, cELF-1 binds well to both of these Ets sites. To further demonstrate the specificity of binding to particular Ets sites, the ability of various cold mutant oligonucleotides to interfere with binding of cELF-1 to the Tie1 P2 Ets sites was tested (FIG. 8D). When both of the Ets site were mutated (Mut 1,2) the oligonucleotides were unable to compete for binding. When the first Ets site was mutated, Mut 1, it competed only weakly with binding of cELF-1 to the Tie1 P2 probe. However, when only the second Ets site was mutated, it competed equally as well as the wild type oligonucleotide suggesting that the first Ets site within this doublet is a higher affinity binding site for cELF-1.

Example 9

The In Vivo Effect of Altered ELF-1 and NERF2 Gene Expression Upon Angiogenesis

To examine the effect of altered ELF-1 and NERF2 gene expression upon angiogenesis, the proangiogenic effect of overexpressing ELF-1 and NERF2 is studied, as well as the antiangiogenic effect of blocking ELF-1 and NERF2 function using either the dominant negative forms of ELF-1 or the NERF1 isoforms. Because the blood vessels of the chicken CAM are easy to visualize, this model of angiogenesis is used to test the effects of expressing these factors upon blood vessel development. An adenoviral method is used to effectively deliver the Ets proteins.

Adenoviral Transfection Method:

We have developed an adenoviral vector (AdCMV-ELF-1) that can express ELF-1 in transfected cells. The generation of the adenovirus was performed as we have done for other genes (Sata, M., et al., 1998. Proc Natl Acad Sci USA 95:1213–7). The human ELF-1 cDNA, under the transcriptional control of the CMV promoter was cloned into the pACCMV-pLpA shuttle vector and cotransfected into human embryonic kidney cells (HEK 293) with the type 5 adenovirus backbone, pJM17.

Similar adenoviral constructs are made for the Ets factor NERF2 and the dominant negative forms of NERF2 and ELF-1. As a control, an adenoviral vector expressing beta-galactosidase or green fluorescent protein (GFP) is used. The adenovirus is injected in a specific area of the chicken CAM at a particular time of development and one can observe the effect of local infection by the virus. The adenovirus is mixed with an adenovirus expressing green fluorescent protein(GFP) which allows us to exactly localize the site of viral infection. In addition, all dominant negative forms of ELF-1 are "tagged" with a Histadine or Myc tag, to allow for immunohistochemical localization. The low cost, fast turn around time, and technical simplicity of these experiments, allows one to quickly evaluate the effect of multiple alternative or mutant constructs in parallel. To accurately assess changes in vessel size and number, the CAMs are fixed and sectioned at different time points after injections.

Example 10

Effect of Delivering Dominant-Negative Forms of NERF2 and ELF-1 Upon Tumor Angiogenesis and Tumor Growth The dominant-negative forms of NERF2 and ELF-1 which have the greatest effect upon limiting angiogenesis in the CAM model are used to test the effect of the dominant-negatives upon tumor angiogenesis and tumor growth.

Methods:

Two mouse tumor models in which blockade of tumor angiogenesis has been shown to limit tumor growth are used.

Model A:

In the first model, the endothelial cell line (Py-4-1), derived from mouse hemangiomas is inoculated into histocompatable mice to induce vascular tumors that resemble hemangiomas (Dubois-Stringfellow, N., et., 1994. Am J Pathol 144:796–806). Administration of angiostatin was recently shown to decrease the tumor volume and vascular proliferation in this model (Lannutti, B. J., et al., 1997. Cancer Res 57:5277–80). Histocompatable mice (B6D2F1, Jackson Laboratories) are then innoculated with Py-4-1 cells. After the tumors have reached a size of 1–2 cm in diameter, they are injected with adenoviruses expressing the dominant negative forms of the selected Ets factors or a control virus. At different time points after injection, tumor specimens are obtained and fixed in 4% paraformaldehyde and embedded in paraffin. Measurements of tumor size are made. To determine blood vessel architecture, deparaffinized sections are stained with endothelial-specific antibodies against von Willebrand factor and CD31(DAKO). Biotinylated secondary antibodies are used against the primary antibody and detected with the streptavidin-Biotin amplified system(Zymed Laboratories).

Model B:

In another model, the breast cancer cell line MDA-MB-435 is injected into the mammary fat pad of nude mice, which provides an orthotopic model of human breast cancer, in which one can measure the size of the primary tumor, and also metastasis(Leone, A., et al., 1993. Oncogene 8:2325–33). The stable transfection of this cell line with thrombospondin was recently shown to reduce primary tumor growth, metastatic potential and angiogenesis in this model (Weinstat-Saslow, D. L., et al., 1994. Cancer Res 54:6504–11). This tumor is injected with the adenoviral constructs and analyze the effects upon tumor angiogenesis and tumor growth as in model A.

Alternatives:

Because the dominant negative forms of the Ets factors are not delivered in an endothelial-specific way it may be necessary to alter the viral delivery method by using an endothelial specific promoter. The adenoviral vector can be redesigned using either the Tie1 or Tie2 promoters to direct expression in an endothelial-specific way.

Example 11

The Effects of Altered NERF2 and Elf-1 Expression Upon Endothelial Function

Antiangiogenic substances inhibit angiogenesis by affecting different aspects of endothelial function. Several recent studies have demonstrated a significant role for the Ets factors in regulating the function of vascular cells including vascular smooth muscle cells and endothelial cells. The expression of Ets-1 is increased in proliferating smooth muscle cells (Naito, S., et al., 1998. Am J Physiol 274:C472–80). Alterations in endothelial adhesion, cell migration, and the formation of capillary tube structures, was observed when dominant-negative forms of Ets1 were overexpressed in endothelial cells (Mattot, V., et al., 2000. Oncogene 19:762–72).

To further define the role of ELF-1 and NERF2 in determining endothelial function, the effect of altered ELF-1 and NERF2 expression on several aspects of endothelial function is studied.

Methods

Two approaches are used to assess the effect of altering NERF2 and ELF-1 expression in endothelial cells.

In the first approach the cDNA encoding the ets factors NERF2 and ELF-1 or their respective dominant-negative forms are subcloned into the PCINeo expression vector (Promega) containing the Neomycin resistance gene. Endothelial cell lines(Py-4-1 or C166) are stably transfected with these constructs. Single clones are isolated by dilution of the initial transfected cells into 96-well plates. For rapid screening, they are characterized by Northern blot analysis and then by Western blotting, to demonstrate expression of the gene and protein. Constructs containing truncated forms of the ets factors have cMYC tags at the 3'end to allow detection of the synthesized protein by Western blot analysis. The empty expression vector are used as a control. This characterization is critical to ensure that the correct protein is expressed.

As a second approach primary endothelial cells(HUVECs or HAECs obtained from Clonetics) are transfected with the adenoviral constructs containing the different forms of the Ets factors or transfected with the control virus and evaluate the effects on endothelial function. The following parameters of endothelial cell function are analyzed.

1. Cell Proliferation:

Adenovirally transfected or cells from individual stably transfected clones are plated at a low density and cell number followed over time. Alternatively, cells are serum starved for 12 hours and then supplemented for 24 hours with serum or growth factors(bFGF and VEGF). At the time of serum supplementation, BrdU(10 mmol/L) or $^3$H-thymidine is added to the media. Cells are washed after an overnight incubation and proliferation is determined by measuring 3H-thymidine incorporation into the cells, or proliferation is measured by the BrdU proliferation assay (Boehringer-Mannheim) according to the manufacturer's recommendations.

2. Cell Migration:

To assess whether endothelial migration is affected in adenovirally transfected or stably transfected clones a migration assay is performed using a chemotaxis chamber (Neuroprobe #AA12). The endothelial cells are grown overnight in the presence of a fluorescent marker, DiI (5 ug/ml). The migration chamber is coated with gelatin and then media containing the chemotactic agent (e.g. 25 ng/ml FGF) is added. A polycarbonate membrane is then placed over this media in each well and secured with a silicone gasket. The endothelial cell clones are then added in equal cell numbers to separate wells over the membrane. After a 4 hour incubation at 37° C. and 5% CO2, the chamber is dismantled and each membrane fixed in 5% Formaldehyde in PBS, and then washed in PBS. Cells on the seeding surface are scraped off with a cell scraper. To determine the number of cells that have entered the membrane, cells are visualized and their number counted with a fluorescence microscope.

3. Cell Adhesion:

These studies are performed by plating cells in calcium and magnesium free PBS and 1% heat-denatured BSA. The endothelial cells are trypsinized, resuspended in media with 0.5% FBS, and plated at $2.0 \times 10^4$ cells per well and incubated at 37° C. for 60 minutes. Nonadherent cells are removed and the adherent cells are detected by trypsinization and counting the cells in the coulter counter. Alternatively, the cells are incubated with 6 mg/ml p-nitrophenylphosphate in 50 mM NaAcetate(pH 5.0)m 1% triton X-100, for 1 h followed by the addition of 1NaOH and the absorbance determined at 405 nm in an ELISA plate reader.

Example 12

Expression of ELF-1 in the Presence of Angiogenic Substances

To further test the ability of angiogenic substances to induce ELF-1 expression in endothelial cells, and in particular in HUVECs and HAECS which do not express ELF-1 under normal culture conditions, endothelial cells are stimulated with bFGF or VEGF, and RNA is isolated from the endothelial cells at different time points and at different concentrations of angiogenic growth factors using the RNAeasy method (Qiagen).

Northern Blot Analysis:

10 to 15 μg of total RNA are transferred to Biotrans nylon membranes (ICN Pharmaceuticals), and hybridized with 32P-labeled cDNA probes which have been made with random primer labeling (Boehringer). The blots are prehybridized in QuickHyb solution (Stratagene) at 68° C. for 30 minutes and then hybridized with the probe, which is boiled together with sheared salmon sperm DNA, and added to the prehybridization solution at a concentration of $1.25 \times 10^6$ CPM per ml of hybridization solution. After hybridization for 60 minutes at 68° C., the blots are washed with increasingly stringent solutions containing SSC and SDS, and increasing the temperature to 60° C. After washing, the blots are exposed on Kodak film. Because the transcription factors are expressed at relatively low levels, they are not easily detectable by northern blot analysis, we will also compare differences in expression by semi-quantitative RT-PCR, or by a more quantitative approach with RNAse protection.

Semiquantitative PCR:

Single stranded cDNA is synthesized from 2 μg of total RNA with oligo(dT) 12–18 priming, using the Moloney murine leukemia virus reverse transcriptase (Gibco). Sequence specific primers are used together with the Taq polymerase(Promega) to amplify representative fragments corresponding to each gene of interest. GAPDH are used as an internal control. PCR will be performed using 1 min for denaturation at 94° C., 1 min annealing at 58° C., and 2 min for extension at 72° C., for a total of 30 cycles.

RNase Protection Assay:

(Ambion RPAII) 10 to 15 μg of total RNA are hybridized with $10^5$ CPM of an ELF-1 antisense RNA probe and hybridized overnight at 45° C. The samples are then treated with RNase for 30 min. The protected fragments are ethanol precipitated and separated out on a 5% polyacrylamide gel, with RNA molecular weight markers. The details of the ELF-1 antisense probe is as previously described (Oettgen, P., et al., 1996, Mol. Cell. Biol. 16:5091106).

Example 13

Analysis of ELF-1 in Embryonic Stem Cell Differentiation Models

A number of ES cell differentiation models have been developed to evaluate hematopoietic lineage differentiation. However, in order to investigate the potential factors contributing to both hematopoiesis and vasculogenesis, we have selected to study ES cell differentiation models where endothelial as well as hematopoietic progenitors are identified in one, and where vascular structures are formed in another.

In the first ES cell culture system, ES cells derived from day 7.5–8.5 mouse embryos are grown on type IV collagen coated dishes(Nishikawa, S. I., et al., 1998. Development 125:1747–57). After 4 days of culture, Flk-1 positive cells, with the potential to develop into hematopoietic or endothelial cells can be separated by flow cytometry. When these cells are cultured on type IV collagen coated dishes supplemented with a mixture of recombinant growth factors, including VEGF, IL-3, and Stem Cell Factor, they give rise to cells of endothelial lineage (VE-cadherin +), erythroid lineage (Ter 119+), and other hematopoietic lineages (CD45+), after an additional three days of culture (See figure)(Nishikawa, S. I., et al., 1998. Development 125:1747–57). This model is used to sort cells using combinations of FITC, phycoerythrin, and biotin conjugated rabbit anti-mouse antibodies directed against Flk1, VE-cadherin, PECAM, E-cadherin, and CD45 (Pharmingen), which can be separated by flow cytometry. We will culture mouse ES cells in this fashion, and separate the cells according to these lineages, and determine the expression of ELF-1 in these cells, by extracting RNA from the subpopulations, and performing RT-PCR or RNase protection as above.

In another model of ES cell differentiation, 129/Sv-derived ES cells are grown and maintained in an undifferentiated state on gelatin coated dishes in the presence of LIF (Gibco BRL) at $10^3$ U/ml, and in the absence of a feeder layer. To initiate ES cell differentiation, cells are trypsinized and plated in 1% methylcellulose containing media. Over the next several days the expression time dependent expression of markers including Flk-1, PECAM, Tie1 and Tie2, VE-cadherin is seen, from as early as 3 to 4 days (Vittet, D., et al., 1996. Blood 88:3424–31). The development of vascular structures and expression of vascular-specific genes are enhanced by the administration of angiogenic substances such as VEGF in the culture medium. The ES-derived embryoid bodies are harvested at selected time points, and the expression of the vascular specific markers and ELF-1 are determined. Alternatively, to better characterize the expression of these genes in relationship to the vascular structures, the embryoid bodies are fixed, and the expression of these genes are determined by in situ hybridization. Colocalization with vascular-specific genes is determined by immunohistochemistry using ELF-1 specific antibodies and to vascular-specific genes, which is performed as outlined above.

The effect of aberrant expression of ELF-1 upon differentiation is determined. Several factors have been recently shown to alter hematopoietic differentiation in ES cell model systems when aberrantly expressed (Helgason, C. D., et al., 1996. Blood 87:2740–9; Levinson-Dushnik, M., and N. Benvenisty. 1997. Mol Cell Biol 17:3817–22; Sorio, C., et al., 1997. Blood 90:49–57). In brief, the cDNAs encoding full-length and dominant negative forms of ELF-1 are sublcloned into the PCI Neo vector (Promega) under the control of a PGK-1 promoter, which is known to be active in ES cells. ES cells are transfected by electroporation, and stably expressing ES cells will be selected with G418. Dominant negative forms either encode the DNA binding domain or the transactivation domain with a c-myc tag at the end. Expression of ELF-1 is confirmed by RT-PCR, and expression of the ELF-1 protein or truncated forms are confirmed by Western blot analysis using an ELF-1 specific antibody or an antibody to the c-myc epitope. These clones are then allowed to differentiate in the same in vitro models as above, and the effect of altered ELF-1 expression on embryonic stem cell differentiation is determined.

Alternatives:

Cells from the different lineages from the transgenic animals overexpressing ELF-1 are isolated as outlined above. If ELF-1 can alter the differentiation of stem cells it is expected that there will be significant differences in the percentage or number of cells of the different lineages.

Example 14

Altered Expression of ELF-1 is Associated with Altered Expression of Vascular-Specific Genes We have shown that ELF-1 gene expression is upregulated in certain endothelial cells in response to angiogenic substances. To assess marked differences in expression, the expression of a number of vascular specific genes is assessed by RT-PCR. Some of the endothelial specific genes upregulated by these Ets factors include Tie1, Tie2, and Flt-1. Furthermore, a number of endothelial specific genes have been shown to be upregulated during angiogenesis or in response to angiogenic signals. Thus, the Ets factor ELF-1 might up regulate the transcription of genes upregulated during angiogenesis or in response to angiogenic substances. Some of the candidate genes which are upregulated in response to angiogenic stimuli include several integrins, including $\alpha_v\beta_3$, $\alpha_1\beta_1$, and $\alpha_1\beta_2$, osteopontin, and plasminogen activators (Senger, D. R., et al., 1997. Proc Natl Acad Sci USA 94:13612–7; Senger, D. R., et al., 1996. Am J Pathol 149:293–305). In addition, a number of functionally important Ets binding sites have been found in the regulatory regions of a number of vascular-specific genes including VE-cadherin, von Willebrand factor, as well as other genes important for vascular function including PDGF and the matrix metalloproteinases MMP-1 and MMP-3 (Buttice, G., et al. Oncogene 13:2297–306; Gory, S., et al., 1998. J Biol Chem 273:6750–5; Kamura, T., et al., 1997. J Biol Chem 272:11361–8; Khachigian, L. M., et al., 1994. J Biol Chem 269:22647–56; Schwachtgen, J. L., et al., 1997. Oncogene 15:3091102). Oligonucleotide primers are designed for each of these genes, and differences in expression in endothelial clones over expressing selected Ets factors are screened in comparison to clones containing the empty expression vector.

Example 15

The In Vivo Effect of Altered ELF-1 Gene Expression

We have shown that altered NERF gene expression leads to abnormalities in endothelial tube cell formation. To examine the effect of altered ELF-1 gene expression upon vasculogenesis, these studies are extended in transgenic experiments by using the Tie1 and Tie2 regulatory elements to direct ELF-1 gene expression in a vascular-specific manner. Because aberrant ELF-1 gene expression may be lethal in the developing embryo, an inducible expression system as an alternative to the standard transgenic approach is used.

Methods:

Transgenic Vectors:

The regulatory elements for the Tie1 and Tie2 genes which have been previously shown to direct vascular specific gene expression for the transgenic experiments are used. (Korhonen, J., et al., 1995. Blood 86:1828–35; Schlaeger, T. M., et al., 1997. Proc Natl Acad Sci USA 94:3058–63). These regulatory elements have been subcloned into the PBS multiple cloning vector (Promega) to generate a Tie1 and Tie2 specific vector. The entire cDNA encoding ELF-1 or dominant negative forms of ELF-1 are inserted followed by the SV40 late gene termination signals, into the Tie1 and Tie2 constructs. These constructs are digested with the unique restriction sites NotI and KpnI, and run on an agarose gel to separate the vector from the rest of the construct. The Tie1-ELF-1 and Tie2-ELF-1 fragments are purified using sodium iodide and silica beads (Gene Clean: Bio101), and equilibrated with injection buffer (10 mM Tris(pH 7.0), 0.1 mM EDTA).

Hybridization Analysis:

To determine transgene incorporation, genomic DNA are prepared from tail biopsies, which are digested with appropriate restriction endonucleases, and run on 1% agarose gels. DNA is transferred to nylon membranes and crosslinked by UV irradiation. Hybridization is performed with a human ELF-1 cDNA probe using quickHyb solution(Stratagene).

Transgene Expression:

To demonstrate the expression of the transgene in mouse embryos harvest RNA from mouse embryos derived from two independent transgenes is used, and RT-PCR is performed using human ELF-1 specific primers, which we have determined not recognize the mouse sequences.

Whole Mount Immunohistochemistry:

To evaluate the effect of ELF-1 overexpression on vascular development, the developing vasculature in mouse embryos is localized at different stages of development expressing the ELF-1 transgene, with PECAM antibodies. Mouse embryos are isolated and fixed in 4% paraformaldehyde in PBS at 4° C. overnight. Fixed embryos are dehydrated in series of methanol. The dehydrated embryos are bleached in 5% hydrogen peroxide in methanol for 4–5 hours at room temperature, and washed in methanol. The bleached embryos are rehydrated and blocked in PBSMT (3% instant skim milk, 0.1% Triton X-100, PBS). The embryos are incubated with a 1:10 dilution of the MEC13.3 monoclonal antibody to mouse PECAM (Pharmingen), in PBSMT at 4° C. overnight. The embryos are then washed five times in PBMST, and then incubated with a horseradish peroxidase conjugated goat anti-rat antibody (DAKO) in PBMST overnight at 4° C. After rinsing 5 times in PBSMT, the embryos are put in PBT(0.2% BSA, 0.1% Triton X-100, PBS), and stained with the peroxidase substrate DAB (0.3 mg/dl) in PBT for 10 to 20 minutes and washing with PBT. The embryos are then post-fixed in 2% paraformaldehyde, 0.1% glutaraldehyde in PBS, then embedded in wax and multiple saggital and coronal sections made. This analysis allows comparison of both embryonic and extra-embryonic blood vessel development at different stages.

Alternatives:

As an alternative, to allow for delayed changes in ELF-1 expression, at later stages of vascular development, an inducible expression system can be used. One such system is the tetracycline-responsive system (Gossen, M., and H. Bujard. 1992. Proc Natl Acad Sci USA 89:5547–51; Gossen, M., et al., 1995. Science 268:1766–9). In this system, the tetracycline-sensitive transactivator (tTA) is formed by fusion of the activating domain of VP16 and the *E. coli* tetracycline repressor protein (TetR) amd is used to activate transcription from a promoter containing the tetracycline operator sequences. This interaction is suppressed by non-toxic amounts of tetracycline, whereas activation of the promoter requires tetracycline withdrawal and results in up to 300 fold induction of the gene of interest. The tetracycline-sensitive transactivator(tTA) is first introduced into a transgenic line under the control of a tissue specific promoter, such as Tie1 or Tie2. Another transgenic line is made in which contains the gene of interest (e.g. ELF-1) under the control of the tetracycline response element (TRE). Homozygous mice containing each construct are then crossed in the presence of tetracycline. The effects of endothelial-specific gene expression of ELF-1 can then be assessed by simply stopping tetracycline administration at different time points. If altered ELF-1 expression results in significant defects in vasculogenesis, this inducible system may provide excellent models for defects in vasculogenesis at different stages of development.

Example 16

Inhibition of Angiogenesis In Vivo in the Chicken CAM

We have demonstrated that overexpression of selected Ets Factors in ECV endothelial cells alters the ability to form tubes in an in vitro Matrigel model. An in vivo model of angiogenesis, namely the chorioallantoic membrane of the chicken, which has a rich blood vessel network that develops over a period of about two weeks is used. Furthermore, we have demonstrated that the expression of cELF-1 is enriched in the developing blood vessels of the CAM. Therefore by altering or inhibiting the activity of this Ets factor in vivo, this will similarly alter endothelial interactions and angiogenesis.

Experimental Approach:

One approach to altering gene expression in the developing chicken is through the use of replication-competent retroviral vectors. Delivery of genes in this manner can result in marked alterations in developmental signals and developmental defects which provide important clues as to the normal function of selected genes (Kengaku, M., et al., 1998. Science 280:1274–7). By varying the infection, protocol these vectors are used to express genes at very early stages in development or at a specific time and location later in development. The use of replication-competent virus allows for the virus to be injected in a specific area and to observe the effect of the gradual infection of the surrounding cells by the virus. The high efficiency of the viral promoter has allowed for gene inactivation by antisense RNA expression. The low cost, fast turn around time, and technical simplicity of these experiments, allows one to quickly evaluate the effect of multiple alternative or mutant constructs in parallel. For the purpose of the experiments below, the retrovirus is initially injected into localized regions in the chorioallantoic membrane, and monitor for effects on blood vessel development.

Retroviral Constructs:

Having isolated chicken ELF-1, a variety of retroviral constructs are designed to examine both the effect of overexpression of cELF-1, and inhibiting the action of cELF-1 by expressing dominant-negative forms of cELF-1. Dominant negative forms of cELF-1 include the DNA binding domain of cELF-1 alone, lacking the transactivation domain, or a cELF-1 lacking the DNA binding domain. The DNA binding domain alone could possibly inhibit several ets factors since the DNA binding domain is so highly conserved, whereas the remainder of the protein outside of the DNA binding domain might be expected to have a more restricted effect, since it shares little homology with most other Ets factors. The selected cDNA fragments encoding the complete or mutated Ets factors are individually cloned into the shuttle vector SLAX-13, and are then subcloned into the replication competent retroviral vector RCAS BS AP(Hughes, S. H., et al., 1987. J Virol 61:3004–12). The proper orientation of the constructs are determined by PCR as previously described (Morgan, B., and D. M. Fekete. 1996. Methods in Cell Biology 51: 185–218).

Production of Retrovirus:

For transfection, primary chicken embryo fibroblasts (CEFs) will be isolated from 10 day old chicken embryos. In brief, 4 to 5 embryos devoid of limbs, head and guts, are minced and then trypsinized in a 10 cm dish. Trypsinized cells are separated from larger pieces of tissue, and then grown in 10 cm dishes. Early passage CEFs are used for transfection of the retroviral vectors for each construct using calcium phosphate method. Six μgs of plasmid DNA is diluted in 450 ul of water and added to 50 µl of 2.5M CaCl2. This solution is added dropwise with bubbling to 500 µl of 2×HBS, and incubated at room temperature for 20 minutes. The media is removed from the plates containing CEFs and 1 ml of fresh media is added together with the precipitated DNA. This is allowed to incubate at 37° C. for 4 hours. The media can then be removed, after which 2 ml of 15% glycerol is added for a 90 second incubation, and washed twice with PBS. 10 ml of media is added to the plates and incubated at 37° C. The cells are then passed for a week or more to ensure that the virus spreads through the culture. To test for the percentage of cells infected with the virus, a small aliquot of cells is stained with an antiviral 3C2 antibody (see below). The culture is then amplified in 15 cm plates. After cells become confluent, 12 ml of media containing 1% serum is used to replace media in dishes. After 24 hours, the media is removed, and filtered through a 0.45 µm cellulose acetate filter with a glass fiber prefilter (Costar). Fresh media is added to the plates for an additional harvest. The virus is then concentrated by centrifugation in a Beckman SW28 at 22,000 RPM for 3 hours. The supernatant is removed and the virus resuspended in 100 to 200 µl of residual supernatant, by gentle shaking on a rotating platform on ice.

Titration of the Virus:

Dilutions of the unconcentrated and concentrated virus are made. Primary CEFs are infected with 100 µl of the diluted virus and incubated for 48 hours. The cells are then washed twice with PBS, and fixed with 4% paraformaldehyde for 15 minutes. After washing three times with PBS, the cells are then preblocked with PBST(10% serum, 0.1% triton X-100 in PBS) for 10 minutes. The cells are then stained for 30 minutes with a 1:5 dilution of the primary 3c2 monoclonal anti-MA antibody. After washing 3 times the horse radish peroxidase linked secondary antibody is added at a dilution of 1/250 in PBST. After washing three times, in PBT, detection of positive cells is made using a secondary antibody detection system, e.g. Vecta Stain (Vector Labs).

Confirmation of Transgene Production:

To verify that the virus is producing the transgene of interest, polyclonal antibodies directed against cELF-1 will be used to detect the expression of these factors by Western blot analysis of viral lysates obtained above.

Alternatives:

It is sometimes possible that the inserted transgene is unstable and that as the virus replicates that it loses the transgene. To test for the stability of the insert, individual clones derived from single plaques can be tested for stability of the insert by PCR. If the insert is unstable either a high titer of a replication defective virus is made or alternatively an adenoviral approach is used. (See below).

Injection of Retrovirus into Fertilized Chicken Embryos:

Fertilized white leghorn chicken eggs are received (SPAFAS, Norwich Ct.) at day 0, and incubated at 37° C. For injection, borosilicate glass capillary pipettes (Omega Cat#30-30-0) are prepared using a P-87 micropipette puller (Sutter Instrument Company). A small hole is made in fertilized eggs at different stages of development with a 21 gauge needle and a small window is made with curved scissors. After injection the hole is covered with clear tape. The injection syringe is partially filled with mineral oil containing 1/40 volume 1% Fast Green dye making sure to eliminate bubbles, and then attached to the capillary which is filled with the oil. Then the desired amount of virus is drawn up into the syringe. Injection of high titer virus can be performed into the fertilized embryos into one area of the chicken CAM or a vascular area of the developing embryo, such as the limb bud, under a dissecting microscope with a micromanipulator, and microinjector. The effects of altered expression of cELF-1 is then determined at different time points after infection, with a particular focus on changes in vascular structure in both embryonic and extraembryonic tissues. To enhance visualization of the blood vessels FITC dextran, MW 200,000(Sigma) can be injected into the umbilical vein and allowed to circulate for 5 minutes prior to fixation in 3.7% formaldehyde. After fixation, thick and thin sections of the CAM or embryo are mounted on slides with 90% glycerol in PBS, and blood vessels visualized on our Nikon inverted fluorescence microscope. Images of the blood vessels can be stored using the attached videoimaging camera (Optronics DEI-750).

Alternative Approach:

One approach to efficiently deliver these Ets factors into the chicken CAM is through the use of adenoviral vectors. The replication-defective adenovirus has previously been shown to be an effective means of gene transfer in chickens (Adam, M., et al., 1995. J Gen Virol 76:3153–7). The development of the new adenoviral vectors are performed as we have previously described (Sata, M., et al., 1998. Proc Natl Acad Sci USA 95:1213–7).

Example 17

Synthetic peptides encoding parts of the terminal portion of the DNA binding domain of NERF and ELF-1, that are highly conserved, block the function of binding of ELF-1 to ETS binding sites in the Tie2 promoter that has been identified as being critical for transactivation of the promoter by NERF2 and ELF-1.

EMSA (Electorphoretic Mobility Shift Assay)

Briefly, 20-µL samples containing 2 µL of in vitro-translated products or cell extracts were incubated with a solution containing 32P-labeleddouble-stranded probes (30 000 cpm). Samples were incubated in the presence or absence of increasing amounts of cold competitor (5 or 50 ng) for 15 to 20 minutes at room temperature and run on a 4% polyacrylamide gel (acrylamide-bisacrylamide, 29:1) containing a buffer of 0.25×TBE (22.5 mmol/L Tris borate and 0.5 mmol/L EDTA).

Oligonucleotides used as probes and for competition studies were as follows:

```
Tie2 promoter oligonucleotide           (SEQ ID NO:8)
5'-TGCAAAGGAAACAGGAAAAAGGAACTTAAC-3'

3'-ACGTTTCCTTTGTCCTTTTTCCTTGAATTG-5'
```

In Vitro Translation of ELF-1

Full-length chicken and human ELF-1 cDNA encoding the entire open-reading frames were inserted downstream of the T7 promoter into the Bluescript vector. Coupled in vitro transcription-in vitro translation reactions were performed with 1 µg of plasmid DNA using the TNT reticulocyte lysate kit (Promega) and T7 RNA polymerase as recommended by the manufacturer. The plasmid vector without an insert was used as a control.

Cotransfection Experiments

Cotransfections of 1.5 to 2×105 endothelial cells or 293 HEK cells were performed using 1.75 µg of the reporter-gene construct DNA and 0.75 µg of the expression-vector DNA with Lipofectamine (Gibco BRL). The cells were harvested 16 hours after transfection and assayed for luciferase.

Individual transfections were performed in duplicate and repeated independently in triplicate with similar results.

Figure 11:
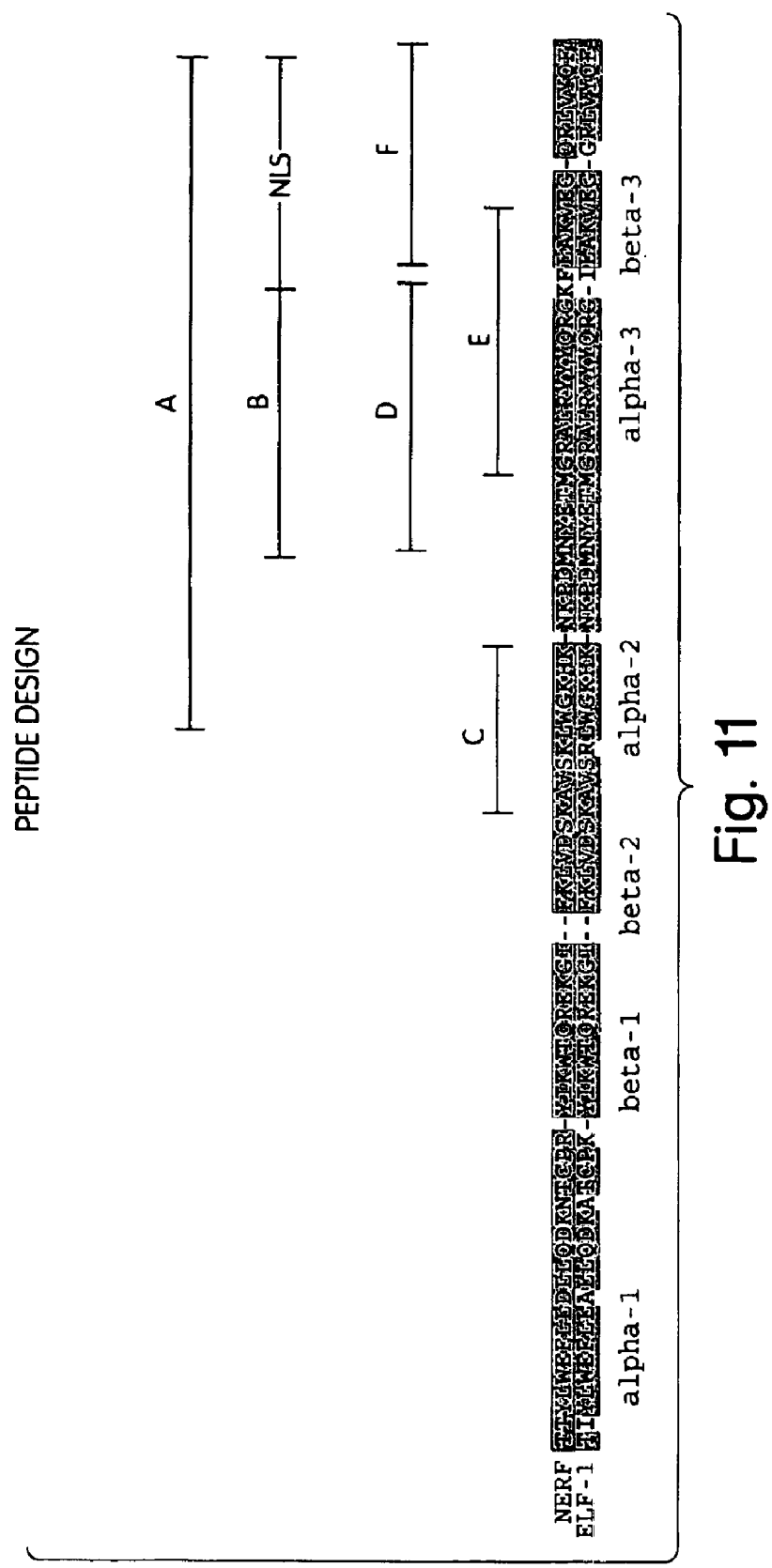
FIG. 11 shows the design of synthetic peptides used in Example 17.
Figure 12:
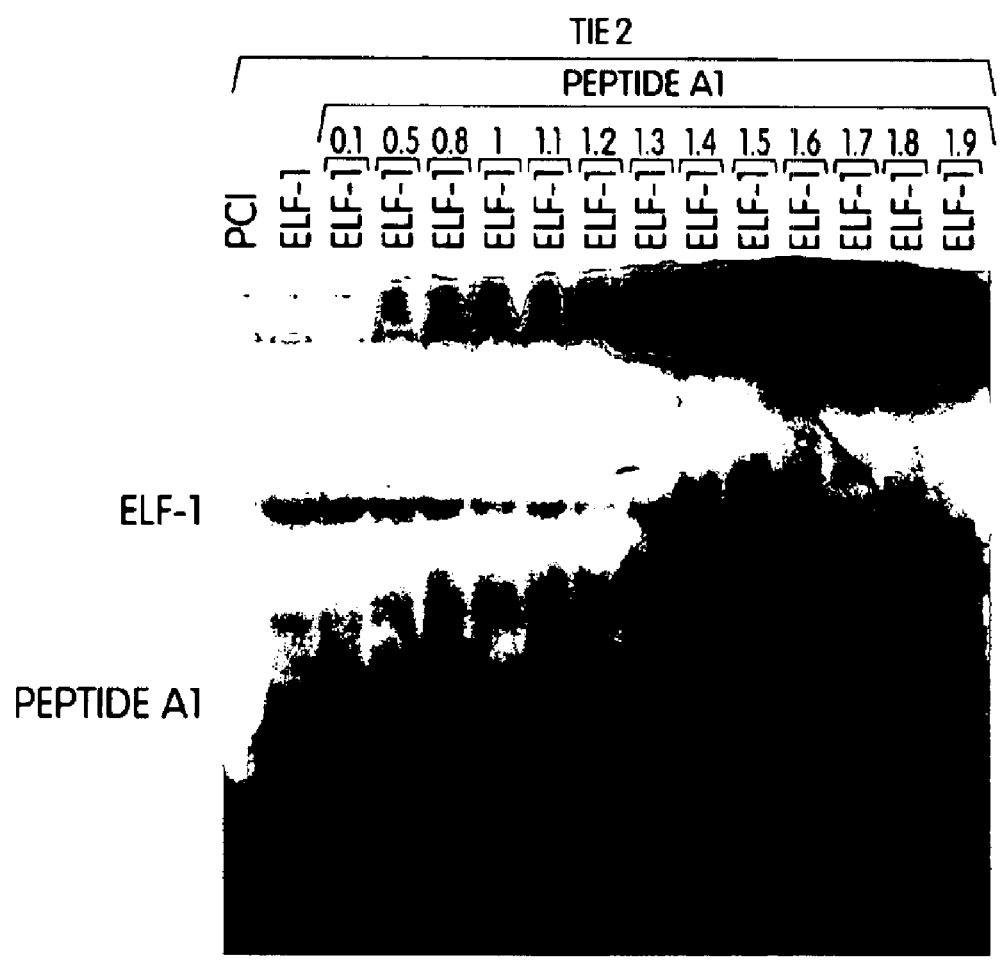
FIG. 12 shows an electrophoretic mobility shift assay using Peptide A1.
Figure 13:
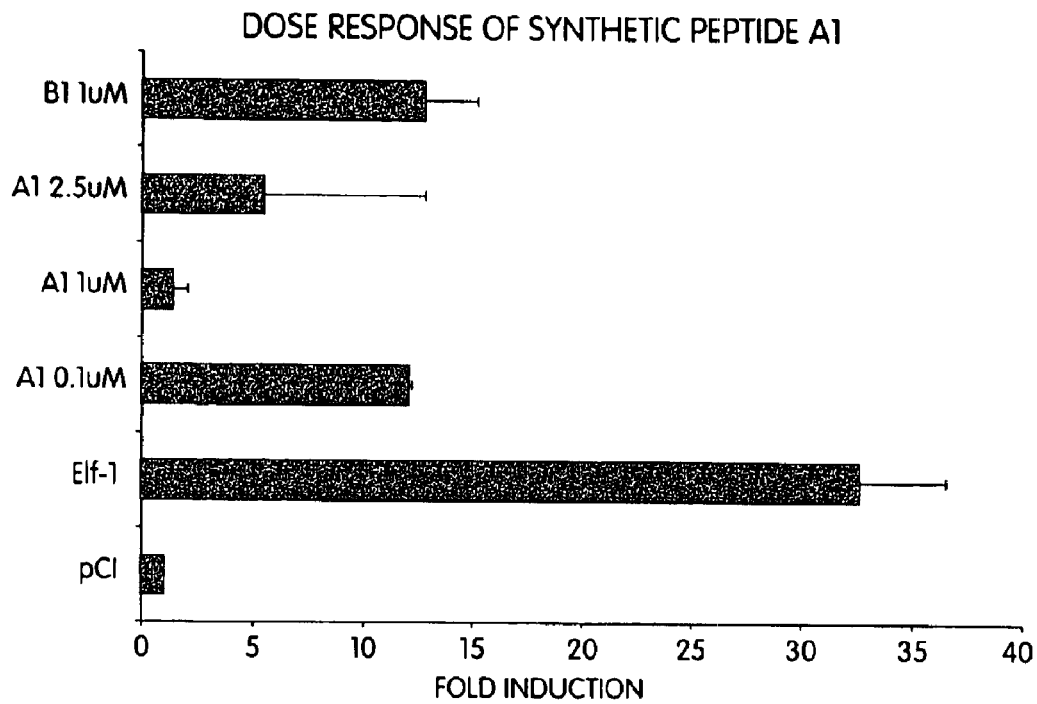
FIG. 13 shows dose response of synthetic peptide A1.
Figure 14:
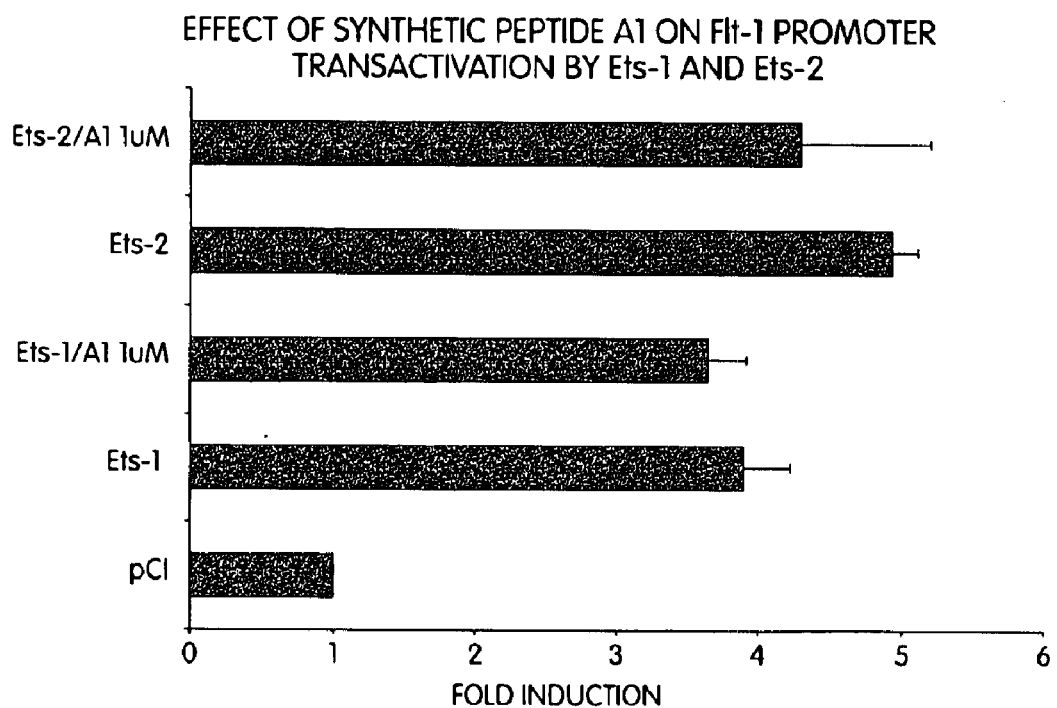
FIG. 14 shows effect of synthetic peptide A1 on Flt-1 promoter transactivation by Ets-1 and Ets-2.

FIG. 11 demonstrates the design of the peptides. Only peptide A, encoding the terminal portion of the DNA binding domain of ELF-1 was capable of blocking the binding of ELF-1 to the ETS binding sites in electrophoretic mobility shift assays, at a concentration of 0.5 to 1.0 micromolar (FIG. 12). Peptide A was also able to block the transactivation of the Tie2 promoter by ELF-1 in transient transfections of 293 HEK cells, at a concentration of 0.1 to 1 micromolar (FIG. 13). Peptide A had not effect on transactivation of the Flt-1 promoter by Ets-1 and Ets-2 (FIG. 14).

The invention has been described in detail with particular references to the preferred embodiments thereof. However, it will be appreciated that modifications and improvements within the spirit and scope of this invention may be made by those skilled in the art upon considering the present disclosure.

The references cited herein are incorporated by reference.

We claim:

1. A method of screening compounds that are capable of increasing blood vessel development and/or endothelial cell differentiation comprising:
   (a) providing cells that do not normally contain a measurable amount of activity of a transcription factor having at least 70% identity to the amino acid sequence of the ETS domain of ELF-1 (amino acid residues 199 to 294 of SEQ ID NO: 2), wherein said cells express at least one vascular specific gene;
   (b) transfecting the cells with a vector comprising nucleic acid encoding a transcription factor having at least 70% identity to the amino acid sequence of the ETS domain of ELF-1 (amino acid residues 199 to 294 of SEQ ID NO: 2), wherein said transcription factor having the ability to transactivate at least one of said vascular specific genes;
   (c) providing to a portion of the cells a compound to be screened;
   (d) not providing to a control portion of the cells the compound to be screened;
   (e) measuring the expression of the vascular-specific genes transactivated by the transcription factor in the cells; and
   (f) comparing the amount of expression of the vascular-specific genes transactivated by the transcription factor in the cells containing the compound with the control portion of cells, wherein expression of the vascular-specific genes in (c) greater than expression of the vascular-specific genes in (d) indicates a compound that increases blood vessel development and/or endothelial cell differentiation.

2. The method according to claim 1, wherein blood vessel development comprises angiogenesis.

3. The method according to claim 1, wherein blood vessel development comprises vasculogenesis.

4. The method according to claim 1, wherein endothelial differentiation comprises development of endothelial cells from pluripotent stem cells.

5. The method according to claim 1, wherein the transcription factor comprises ELF-1, a NERF isoform or MEF.

6. The methods according to claim 5, wherein the transcription factor comprises NERF 2A or NERF 2B.

7. The method according to claim 1, wherein the cells comprise endothelial cells or embryonic stem cells.

8. The method according to claim 7, wherein the endothelial cells are selected from human umbilical vein endothelial cells (HUVECs), human aortic endothelial cells (HAEC), dermal endothelial cells or coronary endothelial cells.

9. The method according to claim 1, wherein the compound comprises a small molecule, peptide, or dominant negative mutant of the transcription factor.

10. The method according to claim 1, wherein the vascular-specific gene is the Tie1 gene, Tie2 gene, FLK-1 gene, or FLT-1 gene.

11. A method of screening compounds that are capable of decreasing blood vessel development and/or endothelial cell differentiation comprising:
   (a) providing cells which do not normally contain a measurable amount of activity of a transcription factor which has at least 70% identity to the amino acid sequence of the ETS domain of ELF-1 (amino acid residues 199 to 294 of SEQ ID NO: 2), wherein said cells express at least one vascular specific gene;
   (b) transfecting the cells with a vector comprising nucleic acid encoding a transcription factor having at least 70% identity to the amino acid sequence of the ETS domain of ELF-1 (amino acid residues 199 to 294 of SEQ ID NO: 2) wherein said transcription factor having the ability to transactivate at least one of said vascular specific genes;
   (c) providing to a portion of the cells a compound to be screened;
   (d) not providing to a control portion of the cells the compound to be screened;
   (e) providing a proangiogenic compound to the cells in (c) and (d);
   (f) measuring the expression of the vascular-specific genes transactivated by the transcription factor in the cells; and
   (g) comparing the amount of expression of the vascular-specific genes transactivated by the transcription factor in the cells containing the compound with the control portion of cells, wherein expression of the vascular-specific genes in (c) less than expression of the vascular-specific genes in (d) indicates a compound that decreases blood vessel development and/or endothelial cell differentiation.

12. The method according to claim 11, wherein blood vessel development comprises angiogenesis.

13. The method according to claim 11, wherein blood vessel development comprises vasculogenesis.

14. The method according to claim 11, wherein endothelial differentiation comprises development of endothelial cells from pluripotent stem cells.

15. The method according to claim 11, wherein the cells comprise endothelial cells or stem cells.

16. The method according to claim 15, wherein the cells are selected from human umbilical vein endothelial cells (HUVECs), human aortic endothelial cells (HAEC), dermal endothelial cells or coronary endothelial cells.

17. The method according to claim 11, wherein the compound comprises a small molecule, peptide, or dominant negative mutant of the transcription factor.

18. The method according to claim 11, wherein the vascular-specific gene is the Tie1 gene, Tie2 gene, FLK-1 gene, or FLT-1 gene.

19. The method according to claim 11, wherein the proangiogenic compound is beta fibroblast growth factor (bFGF), vascular endothelial cell growth factor (VEGF), endothelial cell growth factor (EGF), hepatocyte growth factor (HGF), interleukin-8 (IL-8), or angiopoietin-1.

20. A method of screening compounds that are capable of decreasing blood vessel development and/or endothelial cell differentiation comprising:
   (a) providing cells which normally contain a measurable amount of activity of a transcription factor having at least 70% identity to the amino acid sequence of the ETS domain of ELF-1 (amino acid residues 199 to 294 of SEQ ID NO: 2), wherein said cells express at least one vascular specific gene;
   (b) providing to a portion of the cells a compound to be screened;
   (c) not providing to a control portion of the cells the compound to be screened;
   (d) providing a proangiogenic compound to the cells in (b) and (c);
   (e) measuring the expression of the vascular-specific genes transactivated by the transcription factor in the cells; and
   (f) comparing the amount of expression of the vascular-specific genes transactivated by the transcription factor in the cells containing the compound with the control portion of cells, wherein expression of the vascular-specific genes in (b) less than expression of the vascular-specific genes in (c) indicates a compound that decreases blood vessel development and/or endothelial cell differentiation.

21. The method according to claim 20, wherein blood vessel development comprises angiogenesis.

22. The method according to claim 20, wherein blood vessel development comprises vasculogenesis.

23. The method according to claim 20, wherein endothelial differentiation comprises development of endothelial cells from pluripotent stem cells.

24. The method according to claim 20, the cells comprise cells from blood vessels in CAM, tumor cell angiogenesis in nude mice.

25. The method according to claim 20, wherein the compound comprises a small molecule, peptide, or dominant negative mutant of the transcription factor.

26. The method according to claim 20, wherein the vascular-specific gene is the Tie1 gene, Tie2 gene, FLK-1 gene, or FIT-1 gene.

27. The method according to claim 20, wherein the proangiogenic compound is beta fibroblast growth factor (bFGF), vascular endothelial cell growth factor (VEGF), endothelial cell growth factor (EGF), hepatocyte growth factor (HGF), interleukin-8 (IL-8), or angiopoietin-1.

* * * * *

SEQUENCE LISTING

<160> NUMBER OF SEQ ID NOS: 13

<210> SEQ ID NO 1
<211> LENGTH: 627
<212> TYPE: PRT
<213> ORGANISM: Homo sapiens

<400> SEQUENCE: 1

```
Met Ala Ala Val Val Gln Gln Asn Asp Leu Val Phe Glu Phe Ala Ser
 1               5                  10                  15

Asn Val Met Glu Asp Glu Arg Gln Leu Gly Asp Pro Ala Ile Phe Pro
            20                  25                  30

Ala Val Ile Val Glu His Val Pro Gly Ala Asp Ile Leu Asn Ser Tyr
        35                  40                  45

Ala Gly Leu Ala Cys Val Glu Glu Pro Asn Asp Met Ile Thr Glu Ser
    50                  55                  60

Ser Leu Asp Val Ala Glu Glu Ile Ile Ile Asp Asp Asp Asp Asp Asp
65                  70                  75                  80

Ile Thr Leu Thr Val Glu Ala Ser Cys His Asp Gly Asp Glu Thr Ile
                85                  90                  95

Glu Thr Ile Glu Ala Ala Glu Ala Leu Leu Asn Met Asp Ser Pro Gly
            100                 105                 110

Pro Met Leu Asp Glu Lys Arg Ile Asn Asn Asn Ile Phe Ser Ser Pro
        115                 120                 125

Glu Asp Asp Met Val Val Ala Pro Val Thr His Val Ser Val Thr Leu
    130                 135                 140

Asp Gly Ile Pro Gly Val Met Glu Thr Gln Gln Val Gln Glu Lys Tyr
145                 150                 155                 160

Ala Asp Ser Pro Gly Ala Ser Ser Pro Glu Gln Pro Lys Arg Lys Lys
                165                 170                 175

Gly Arg Lys Thr Lys Pro Pro Arg Pro Asp Ser Pro Ala Thr Thr Pro
            180                 185                 190

Asn Ile Ser Val Lys Lys Lys Asn Lys Asp Gly Lys Gly Asn Thr Ile
        195                 200                 205

Tyr Leu Trp Glu Phe Leu Leu Ala Leu Leu Gln Asp Lys Ala Thr Cys
    210                 215                 220

Pro Lys Tyr Ile Lys Trp Thr Gln Arg Glu Lys Gly Ile Phe Lys Leu
225                 230                 235                 240

Val Asp Ser Lys Ala Val Ser Arg Leu Trp Gly Lys His Lys Asn Lys
                245                 250                 255

Pro Asp Met Asn Tyr Glu Thr Met Gly Arg Ala Leu Arg Tyr Tyr Tyr
            260                 265                 270

Gln Arg Gly Ile Leu Ala Lys Val Glu Gly Gln Arg Leu Val Tyr Gln
        275                 280                 285
```

```
Phe Lys Glu Met Pro Lys Asp Leu Ile Tyr Ile Asn Asp Glu Asp Pro
    290                 295                 300

Ser Ser Ser Ile Glu Ser Ser Asp Pro Ser Leu Ser Ser Ser Ala Ser
305                 310                 315                 320

Asn Arg Asn Gln Thr Ser Arg Ser Arg Val Ser Ser Ser Pro Gly Val
                325                 330                 335

Lys Gly Gly Ala Thr Thr Val Leu Lys Pro Gly Asn Ser Lys Ala Ala
            340                 345                 350

Lys Pro Lys Asp Pro Val Glu Val Ala Gln Pro Ser Glu Val Leu Arg
        355                 360                 365

Thr Val Gln Pro Thr Gln Ser Pro Tyr Pro Thr Gln Leu Phe Arg Thr
    370                 375                 380

Val His Val Val Gln Leu Phe Thr Arg Val His Val Met Gln Pro Val
385                 390                 395                 400

Gln Ala Val Pro Glu Gly Glu Ala Ala Arg Thr Ser Thr Met Gln Asp
                405                 410                 415

Glu Thr Leu Asn Ser Ser Val Gln Ser Ile Arg Thr Ile Gln Ala Pro
            420                 425                 430

Thr Gln Val Pro Val Val Ser Pro Arg Asn Gln Gln Leu His Thr
        435                 440                 445

Val Thr Leu Gln Thr Val Pro Leu Thr Thr Val Ile Ala Ser Thr Asp
    450                 455                 460

Pro Ser Ala Gly Thr Gly Ser Gln Lys Phe Ile Leu Gln Ala Ile Pro
465                 470                 475                 480

Ser Ser Pro Pro Met Thr Val Leu Lys Glu Asn Val Met Leu Gln Ser
                485                 490                 495

Gln Lys Ala Gly Ser Pro Pro Ser Ile Val Leu Gly Pro Ala Gln Val
            500                 505                 510

Gln Gln Val Leu Thr Ser Asn Val Gln Thr Ile Cys Asn Gly Thr Val
        515                 520                 525

Ser Val Ala Ser Ser Pro Ser Phe Ser Ala Thr Ala Pro Gly Val Thr
    530                 535                 540

Phe Ser Pro Arg Ser Ser Gln Leu Val Ala His Pro Pro Gly Thr Val
545                 550                 555                 560

Ile Thr Ser Val Ile Lys Thr Gln Glu Thr Lys Thr Leu Thr Gln Glu
                565                 570                 575

Val Glu Lys Lys Glu Ser Glu Asp His Leu Lys Glu Asn Thr Glu Lys
            580                 585                 590

Thr Glu Gln Gln Pro Gln Pro Tyr Val Met Val Val Ser Ser Ser Asn
        595                 600                 605

Gly Phe Thr Ser Gln Val Ala Met Lys Gln Asn Glu Leu Leu Glu Pro
    610                 615                 620

Asn Ser Phe
625

<210> SEQ ID NO 2
<211> LENGTH: 628
<212> TYPE: PRT
<213> ORGANISM: Gallus gallus

<400> SEQUENCE: 2

Met Ala Ala Val Val Gln Gln Asn Glu Leu Val Phe Glu Phe Ala Ser
  1               5                  10                  15

Asn Val Met Glu Asp Glu Gln Gln Leu Gly Asp Pro Ser Ile Phe Pro
```

-continued

```
                20                  25                  30
Ala Val Ile Val Glu His Val Pro Ser Gly Asp Leu Leu Asn Asn Tyr
                35                  40                  45
Ser Gly Leu Thr Cys Val Asp Glu Pro Ser Asp Met Ile Thr Glu Asn
        50                  55                  60
Ser Leu Asp Val Ala Glu Gln Ile Ile Glu Asp Asp Asp Ile
65                  70                  75                  80
Pro Leu Thr Val Glu Thr Ser Cys His Asn Gly Asp Glu Thr Met Glu
                    85                  90                  95
Thr Ile Glu Ala Ala Glu Ala Leu Leu His Met Asp Ser Pro Gly Pro
                100                 105                 110
Met Leu Asp Glu Lys Arg Ile Thr Ala Met Ile Phe Gly Ser Thr Glu
                115                 120                 125
Asp Glu Asp Ile Val Ala Pro Ile Thr His Val Ser Val Thr Leu Asp
130                 135                 140
Gly Ile Pro Glu Val Glu Val His Gln Ala Pro Asp Pro Tyr Ser
145                 150                 155                 160
Glu Thr Pro Glu Thr Pro Glu Phe Glu Gln Pro Lys Lys Lys Gly
                    165                 170                 175
Lys Lys Pro Lys Pro Ser Arg Pro Glu Ser Pro Thr Thr Thr Pro Asn
                180                 185                 190
Ile Ser Val Lys Lys Asn Lys Asp Gly Lys Gly Asn Thr Ile Tyr
                195                 200                 205
Leu Trp Glu Phe Leu Leu Ala Leu Leu Gln Asp Lys Ala Thr Cys Pro
    210                 215                 220
Lys Tyr Ile Lys Trp Thr Gln Arg Glu Lys Gly Ile Phe Lys Leu Val
225                 230                 235                 240
Asp Ser Lys Ala Val Ser Arg Leu Trp Gly Lys His Lys Asn Lys Pro
                    245                 250                 255
Asp Met Asn Tyr Phe Thr Met Gly Arg Ala Leu Arg Tyr Tyr Gln
                260                 265                 270
Arg Gly Ile Leu Ala Lys Val Glu Gly Gln Arg Leu Val Val Gln Phe
        275                 280                 285
Lys Glu Met Pro Lys Asp Leu Val Tyr Ile Asp Asp Glu Asp Ala Ser
    290                 295                 300
Pro Ser Thr Glu Ser Ser Asp Ser Ser Leu Leu Ser Thr Pro Val Ala
305                 310                 315                 320
Ser Arg Asn Gln Ser Ser Arg Ser Arg Ala Ser Ala Asn Thr Gly Thr
                325                 330                 335
Lys Gly Gly Ser Thr Thr Val Leu Lys Thr Gly Asn Ser Lys Pro Ala
                340                 345                 350
Lys Leu Lys Glu His Val Glu Val Gln Gln Thr Pro Gly Leu
                355                 360                 365
Thr Ser Glu Val Leu Arg Thr Met Gln Ser Thr Gln Pro Val His Pro
        370                 375                 380
Thr Gln Leu Phe Arg Thr Val His Val Met Gln Pro Leu His Thr Leu
385                 390                 395                 400
Thr Glu Gly His Ala Ala Val Thr Ser Asn Val Pro Asp Glu Thr Leu
                    405                 410                 415
Asn Pro Ser Val Gln Asn Ile Arg Thr Leu Gln Thr Pro Thr Gln Val
                420                 425                 430
Pro Val Val Val Ser Pro Gly Asn Gln Gln Leu His Thr Val Thr Leu
                435                 440                 445
```

-continued

```
Gln Thr Val Pro Leu Thr Thr Val Ile Ala Ser Thr Asp Pro Ala Ser
    450                 455                 460

Ala Ala Thr Pro Gln Lys Phe Ile Leu Gln Ala Ile Pro Thr Ser Pro
465                 470                 475                 480

Pro Met Thr Val Leu Lys Glu Asn Val Met Leu Gln Ser Gln Lys Pro
                    485                 490                 495

Val Ser Pro Pro Ser Ser Ile Val Leu Ser Pro Ala Gln Val Gln Gln
                500                 505                 510

Val Leu Thr Ser Ser Val Gln Thr Ile Cys Asn Gly Thr Ala Asn Val
        515                 520                 525

Ala Ser Ser Pro Ser Phe Ala Ala Thr Thr Pro Val Val Thr Phe Ser
    530                 535                 540

Pro Ser Ser Ser Gln Val Ala His Pro Ser Gly Thr Val Ile Thr
545                 550                 555                 560

Ser Val Ile Lys Ala Thr Glu Ala Lys Gln Ile Gly Val Gln Gly Val
                    565                 570                 575

Leu Lys Glu Asp Asp Gly Asp Lys Leu Asp Asp Pro Glu Gln Ser Glu
                580                 585                 590

Gln Arg Phe Gln Gln Gln Pro Phe Val Met Val Val Ser Ser Ser Asn
        595                 600                 605

Ser Phe Pro Ser Asn Ile Gln Ala Lys Gln Glu Asn Glu Pro Leu Glu
    610                 615                 620

Pro Asn Ser Tyr
625

<210> SEQ ID NO 3
<211> LENGTH: 622
<212> TYPE: PRT
<213> ORGANISM: Mus sp.

<400> SEQUENCE: 3

Met Ala Ala Val Val Gln Gln Asn Asp Leu Val Phe Glu Phe Ala Ser
  1               5                  10                  15

Asn Gly Met Glu Asp Glu Gln Gln Leu Gly Asp Pro Ala Ile Phe Pro
                 20                  25                  30

Ala Val Ile Val Glu His Val Pro Gly Ala Asp Ile Leu Asn Ser Tyr
            35                  40                  45

Ala Gly Leu Ala Cys Val Glu Glu Pro Asn Asp Met Ile Thr Glu Asn
        50                  55                  60

Ser Leu Asp Val Ala Glu Glu Ile Ile Ile Asp Asp Asp Asp Ile
 65                  70                  75                  80

Thr Leu Thr Val Glu Ala Ser Cys His Asn Gly Asp Glu Thr Met Glu
                 85                  90                  95

Thr Ile Glu Ala Ala Glu Ala Leu Leu Asn Ile Asp Ser Pro Ser Pro
            100                 105                 110

Pro Val Leu Asp Glu Lys Gln Ile Asn Asn Asn Ile Phe Ser Ser Ser
        115                 120                 125

Glu Asp Asp Ile Val Ala Pro Ile Thr His Val Ser Val Thr Leu
130                 135                 140

Asp Gly Ile Pro Glu Val Met Glu Thr Gln Gln Val Gln Glu Thr Asn
145                 150                 155                 160

Ala Asp Ser Pro Gly Ala Ser Ser Pro Glu Gln Arg Lys Arg Lys Lys
                165                 170                 175

Gly Arg Lys Thr Lys Pro Pro Arg Pro Asp Ser Pro Thr Thr Thr Pro
```

-continued

```
                180                 185                 190
Asn Ile Ser Val Lys Lys Asn Lys Asp Gly Lys Gly Asn Thr Ile
            195                 200                 205
Tyr Leu Trp Glu Phe Leu Leu Ala Leu Leu Gln Asp Lys Ala Thr Cys
            210                 215                 220
Pro Lys Tyr Ile Lys Trp Thr Gln Arg Glu Lys Gly Ile Phe Lys Leu
225                 230                 235                 240
Val Asp Ser Lys Ala Val Ser Arg Leu Trp Gly Lys His Lys Asn Lys
                245                 250                 255
Pro Asp Met Asn Tyr Phe Thr Met Gly Arg Ala Leu Arg Tyr Tyr Tyr
            260                 265                 270
Gln Arg Gly Ile Leu Ala Lys Val Glu Gly Gln Arg Leu Val Val Gln
            275                 280                 285
Phe Lys Glu Met Pro Lys Asp Leu Ile Tyr Ile Asp Glu Asp Pro
290                 295                 300
Ser Ser Ser Ile Glu Ser Ser Asp Gln Ser Leu Ser Ser Thr Thr Ala
305                 310                 315                 320
Ser Ser Arg Asn Gln Ala Asn Arg Ser Arg Val Ser Ser Ser Pro Gly
                325                 330                 335
Ile Lys Gly Gly Ala Ala Thr Ile Leu Lys Pro Gly Asn Ser Lys Ala
            340                 345                 350
Ala Asn Pro Lys Asp Pro Val Glu Val Gly Gln Pro Ser Glu Val Leu
            355                 360                 365
Arg Thr Val Gln Pro Ser Gln Ala Pro Tyr Pro Thr Gln Leu Phe Arg
            370                 375                 380
Thr Val His Val Val Gln Leu Phe Arg Thr Val His Val Met Gln Pro
385                 390                 395                 400
Val Gln Ala Val Pro Glu Glu Ala Thr Ile Ala Ser Thr Met Gln Glu
                405                 410                 415
Glu Ala Ala Asn Ser Ser Val Pro Ser Ile Arg Thr Ile Gln Ala Ser
            420                 425                 430
Thr Gln Val Pro Val Val Ser Pro Gly Asn Gln Gln Leu His Thr
            435                 440                 445
Val Thr Val Pro Leu Thr Thr Val Ile Ala Ser Ile Asp Pro Ser Ser
450                 455                 460
Gly Ala Gly Ser Gln Lys Phe Ile Leu Gln Thr Ile Pro Ser Ser Pro
465                 470                 475                 480
Pro Met Thr Val Leu Lys Glu Asn Val Met Leu Gln Ser Gln Lys Pro
                485                 490                 495
Gly Ser Pro Ser Ile Val Leu Ser Pro Thr Gln Val Gln Val Leu
            500                 505                 510
Thr Ser Asn Val Gln Ser Ile Cys Asn Gly Ala Gly Ser Val Ala Ser
            515                 520                 525
Ala Pro Ser Phe Ser Ala Thr Ala Pro Val Val Thr Phe Ser Pro Arg
            530                 535                 540
Ser Ser Gln Leu Val Ala His Pro Pro Gly Thr Val Ile Thr Ser Val
545                 550                 555                 560
Ile Lys Lys Gln Glu Thr Lys Thr Leu Thr Gln Glu Val Glu Lys Lys
                565                 570                 575
Ala Glu Asp Asp Leu Asn Glu Asp Ala Glu Lys Ser Ala Gln Gln Pro
            580                 585                 590
Gln Pro Tyr Val Met Val Leu Ser Ser Asn Gly Phe Ser Ser Gln
            595                 600                 605
```

```
Val Ala Val Lys Gln Asn Glu Leu Leu Glu Pro Asn Ser Phe
    610             615                 620
```

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4
atggctgctg ttgtccaac                                                    19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
cctgagtgct ctycccat                                                     18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
caaagttgtc atggatgacc                                                   20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
ccatggagaa ggctgggg                                                     18

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 8
tgcaaaggaa acaggaaaaa ggaacttaac                                        30

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Probe

<400> SEQUENCE: 9
actggcttcc tccctttcct gtctc                                             25

<210> SEQ ID NO 10
<211> LENGTH: 24

```
<212> TYPE: DNA
<213> ORGANISM: Artificial Sequence
<220> FEATURE:
<223> OTHER INFORMATION: Description of Artificial Sequence: Probe

<400> SEQUENCE: 10
ccatcatttc ctcttcctcc ccag                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 11
ccatcattta atcttcctcc ccag                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 12
ccatcatttc ctcttaatcc ccag                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Probe

<400> SEQUENCE: 13
ccatcattta atcttaatcc ccag                                              24
```